United States Patent
Träff et al.

(10) Patent No.: US 12,249,031 B2
(45) Date of Patent: Mar. 11, 2025

(54) METHOD FOR GENERATING OBJECTS USING AN HOURGLASS PREDICTOR

(71) Applicant: 3SHAPE A/S, Copenhagen K (DK)

(72) Inventors: Jens Peter Träff, Copenhagen K (DK); Jens Christian Jørgensen, Seattle, WA (US); Alejandro Alonso Diaz, Copenhagen K (DK); Mathias Bøgh Stokholm, Copenhagen K (DK); Asger Vejen Hoedt, Vallensbæk (DK)

(73) Assignee: 3SHAPE A/S, Copenhagen K (DK)

( * ) Notice: Subject to any disclaimer, the term of this patent is extended or adjusted under 35 U.S.C. 154(b) by 0 days.

(21) Appl. No.: 18/390,173

(22) Filed: Dec. 20, 2023

(65) Prior Publication Data
US 2024/0212278 A1   Jun. 27, 2024

Related U.S. Application Data

(63) Continuation of application No. 17/434,205, filed as application No. PCT/EP2020/054852 on Feb. 25, 2020, now Pat. No. 11,887,209.

(30) Foreign Application Priority Data

Feb. 27, 2019   (DK) .............. PA 2019 70132

(51) Int. Cl.
*G06T 17/00*   (2006.01)
*A61C 7/00*   (2006.01)
(Continued)

(52) U.S. Cl.
CPC .............. *G06T 17/20* (2013.01); *A61C 7/002* (2013.01); *A61C 9/0053* (2013.01);
(Continued)

(58) Field of Classification Search
CPC .......... G06T 17/20; G06T 2207/30036; G06T 17/00; G06T 2210/41
See application file for complete search history.

(56) References Cited

U.S. PATENT DOCUMENTS

| | | |
|---|---|---|
| 2004/0135788 A1 | 7/2004 | Davidson et al. |
| 2007/0168152 A1 | 7/2007 | Matov et al. |

(Continued)

FOREIGN PATENT DOCUMENTS

| | | |
|---|---|---|
| CN | 104041036 A | 9/2014 |
| CN | 108364639 A | 8/2018 |

(Continued)

OTHER PUBLICATIONS

Chakravarty R., et al. "Interactive Reconstruction of Monte Carlo Image Sequences using a Recurrent Denoising Autoencoder", ACM Transactions on Graphics, vol. 36, No. 4, Jul. 20, 2017, pp. 1-12, XP058372872.

(Continued)

*Primary Examiner* — Matthew Salvucci
(74) *Attorney, Agent, or Firm* — Buchanan Ingersoll & Rooney PC

(57) ABSTRACT

A computer-implemented method for generating a 2D or 3D object, including training an autoencoder on a first set of training data to identify a first set of latent variables and generate a first set of output data; training an hourglass predictor on a second set of training data, where the hourglass predictor encoder converts a set of related but different training input data to a second set of latent variables, which decode into a second set of output data of the same type as the first set of output data; and using the hourglass predictor (Continued)

to predict a 2D or 3D object of the same type as the first set of output data based on a 2D or 3D object of the same type as the second set of input data.

15 Claims, 12 Drawing Sheets

(51) Int. Cl.
*A61C 9/00* (2006.01)
*A61C 13/00* (2006.01)
*G06T 7/00* (2017.01)
*G06T 9/00* (2006.01)
*G06T 11/00* (2006.01)
*G06T 17/20* (2006.01)
*G06T 19/20* (2011.01)
*G06V 10/774* (2022.01)
*G16H 30/40* (2018.01)

(52) U.S. Cl.
CPC ...... *A61C 13/0004* (2013.01); *A61C 13/0019* (2013.01); *G06T 7/0012* (2013.01); *G06T 9/002* (2013.01); *G06T 11/00* (2013.01); *G06T 17/00* (2013.01); *G06T 19/20* (2013.01); *G06V 10/7747* (2022.01); *G16H 30/40* (2018.01); *G06T 2207/30036* (2013.01); *G06T 2210/41* (2013.01); *G06T 2219/2021* (2013.01)

(56) References Cited

U.S. PATENT DOCUMENTS

| | | |
|---|---|---|
| 2016/0199215 A1 | 7/2016 | Kopelman |
| 2018/0028294 A1 | 2/2018 | Azernikov et al. |
| 2018/0204379 A1 | 7/2018 | Mendoza et al. |
| 2018/0247200 A1 | 8/2018 | Rolfe |
| 2019/0026631 A1 | 1/2019 | Carr et al. |
| 2019/0172555 A1 | 6/2019 | Apte et al. |
| 2020/0202622 A1 | 6/2020 | Gallo et al. |
| 2022/0172430 A1 | 6/2022 | Träff et al. |

FOREIGN PATENT DOCUMENTS

| | | |
|---|---|---|
| CN | 109074512 A | 12/2018 |
| WO | 2013010910 A1 | 1/2013 |
| WO | 2016143022 A1 | 9/2016 |

OTHER PUBLICATIONS

Floater, et al., "Polygonal spline spaces and the numerical solution of the Poisson equation." SIAM Journal on Numerical Analysis, 2016 (month unknown), vol. 54, No. 2, pp. 797-824.

International Search Report (PCT/ISA/210) mailed on Jul. 7, 2020, by the European Patent Office as the International Searching Authority for International Application No. PCT/EP2020/054852.

Meyer, et al. "Discrete differential-geometry operators for triangulated 2-manifolds." Visualization and mathematics III, 2003 (month unknown), pp. 35-57.

Newell, et al., "Stacked Hourglass Networks for Human Pose Estimation", International Conference on Financial Cryptography and Data Security, Sep. 2016, pp. 483-499.

Qi, et al., "PointNet: Deep Learning on Point Sets for 3D Classification and Segmentation", Proceedings of the IEEE Conference on Computer Vision and Pattern Recognition (CVPR), 2017 (month unknown), pp. 652-660.

Tutte, "How to draw a graph", Proceedings of the London Mathematical Society 3.1 1963 (month unknown), pp. 743-767.

Wang, et al., "Multiscale structural similarity for image quality assessment," The Thrity-Seventh Asilomar Conference on Signals, Systems & Computers, 2003, Nov. 2003, pp. 1398-1402 vol. 2.

Zou, et al., "3D-PRNN: Generating Shape Primitives With Recurrent Neural Networks", Proceedings of the IEEE International Conference on Computer Vision (ICCV), 2017 (month unknown), pp. 900-909.

Papadomanolaki et al. "Stacked Encoder-Decoders for Accurate Semantic Segmentation of Very High Resolution Satellite Datasets". IGARSS 2018—38th annual International Geoscience and Remote Sensing Symposium, Jul. 2018, Valencia, Spain. pp. 1-4. hal-01870857. The whole document.

First Office Action issued in Chinese Patent Application No. 202080031435.6, dated Sep. 14, 2023, with English Translation (19 pages).

FIG. 2

200 – Training the autoencoder
- 201 – First set of training input data
- 202 – First encoder
- 203 – First set of latent variables
- 204 – First decoder
- 205 – First set of output data
- 206 – First set of training input data

207 – Training the hourglass predictor
- 208 – Second set of training input data
- 209 – Second encoder
- 210 – Second set of latent variables
- 211 – First decoder
- 212 – Second set of output data
- 213 – Set of training target data

214 – Using the hourglass predictor
- 215 – Third set of input data
- 216 – Second encoder
- 217 – Third set of latent variables
- 218 – First decoder
- 219 – Third set of output data

FIG. 5

500 – Training the autoencoder for crowns/teeth

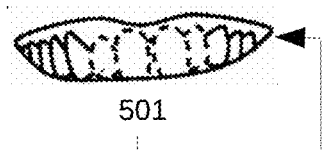
501

↓

502 – matrices of proposed digital 2D images

↓

503 – conv. neural network A

↓ ↓

504 – means    505 – std. dev.

↓ ↓

506 – latent variables, i.e. proposed 2D digital image parametrization

↓

507 – conv. neural network B

↓

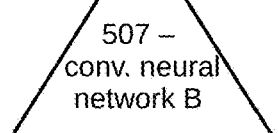

508 – autoencoded matrices of proposed digital 2D images
509 – matrices of proposed digital 2D images

510 – Training the hourglass predictor for proposed digital 2D image given pre-treatment digital 2D image

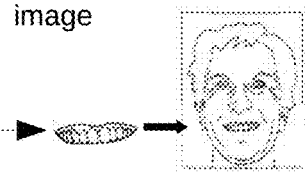
511   512

↓

513 – matrices of matched pre-treatment digital 2D images

↓

514 – conv. neural network C

↓ ↓

515 – means    516 – std. dev.

↓ ↓

517 – latent variables, i.e. matched proposed 2D digital image parametrization

↓

518 – conv. neural network B

↓

519 – matrices of matched proposed digital 2D images
520 – matrices of matched proposed digital 2D images

521 – Predicting proposed digital 2D image for new pre-treatment digital 2D image

522

↓

523 – matrix of new pre-treatment digital 2D image

↓

524 – conv. neural network C

↓ ↓

525 – means    526 – std. dev.

↓ ↓

527 – latent variables, i.e. proposed 2D digital image parametrization

↓

528 – conv. neural network B

↓

529 – matrix of the predicted proposed digital 2D image prediction

↓

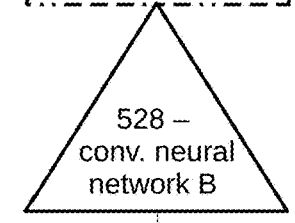
530   531

FIG. 7
700
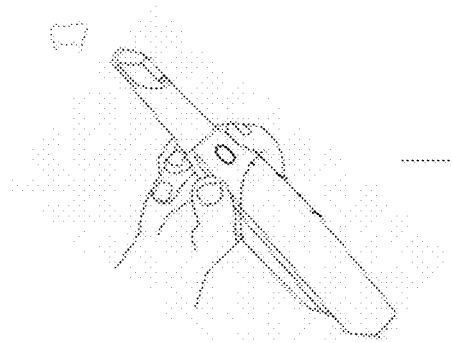
701
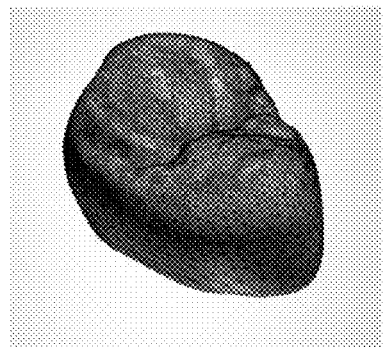
702
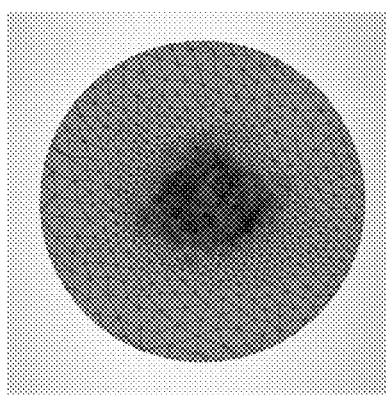
703
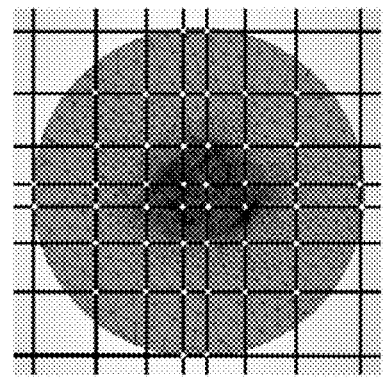
704
$$\begin{pmatrix} a_{11} & a_{12} & a_{13} & \cdots & a_{1m} \\ a_{21} & a_{22} & a_{23} & \cdots & a_{2m} \\ a_{31} & a_{32} & a_{33} & \cdots & a_{3m} \\ \vdots & \vdots & \vdots & \vdots & \vdots \\ a_{n1} & a_{n2} & a_{n3} & \cdots & a_{nm} \end{pmatrix}$$
705
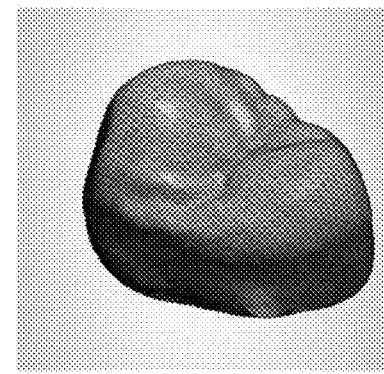

FIG. 8A 800  801  802

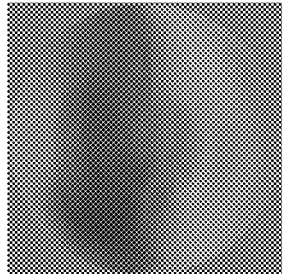 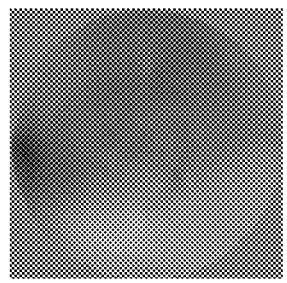 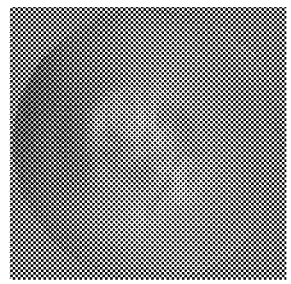

$$\begin{bmatrix} \vdots & & & \\ -0.893 & -0.826 & -0.812 & \ldots \\ -0.795 & -0.729 & -0.719 & \ldots \\ -0.698 & -0.637 & -0.626 & \ldots \\ \vdots & & & \end{bmatrix}$$

804

$$\begin{bmatrix} \vdots & & & \\ -5.709 & -5.962 & -6.273 & \ldots \\ -5.690 & -6.052 & -6.342 & \ldots \\ -5.667 & -6.139 & -6.408 & \ldots \\ \vdots & & & \end{bmatrix}$$

805

$$\begin{bmatrix} \vdots & & & \\ -2.701 & -2.270 & -1.977 & \ldots \\ -2.581 & -2.223 & -1.941 & \ldots \\ -2.491 & -2.177 & -1.919 & \ldots \\ \vdots & & & \end{bmatrix}$$

806

$$\begin{bmatrix} \vdots & & & \\ [-0.893, -5.709, -2.701] & [-0.826, -5.962, -2.270] & [-0.812, -6.273, -1.977] & \ldots \\ [-0.795, -5.690, -2.581] & [-0.729, -6.052, -2.223] & [-0.719, -6.342, -1.941] & \ldots \\ [-0.698, -5.667, -2.491] & [-0.637, -6.139, -2.177] & [-0.626, -6.408, -1.919] & \ldots \\ \vdots & & & \end{bmatrix}$$

FIG. 8C

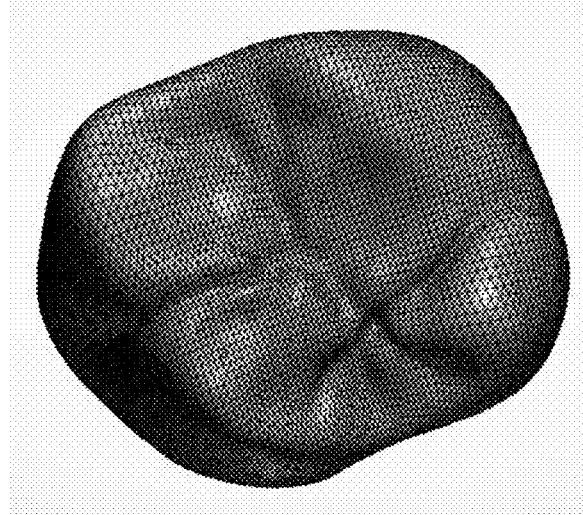

FIG. 10
1001
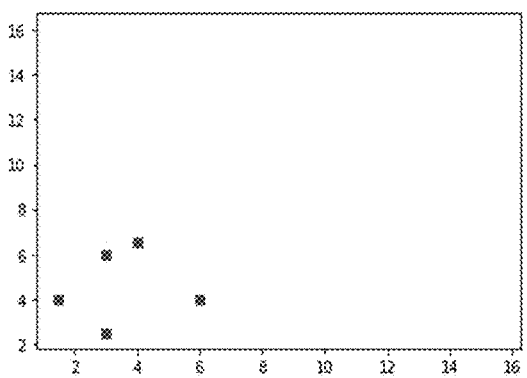
1002
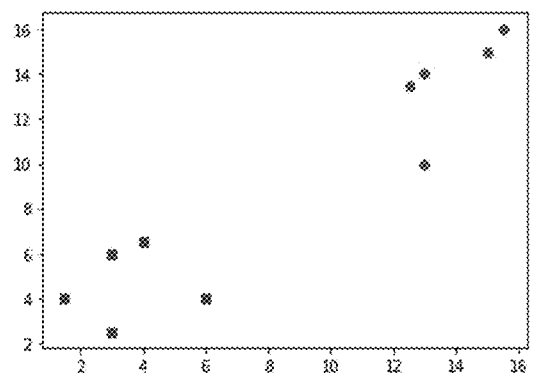
1003
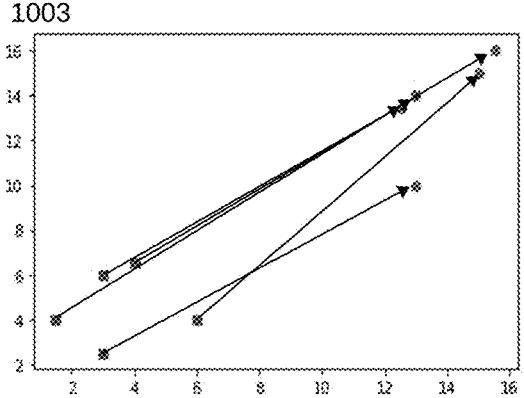
1004
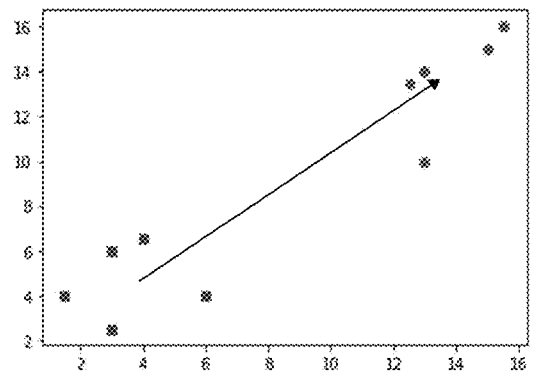
1005
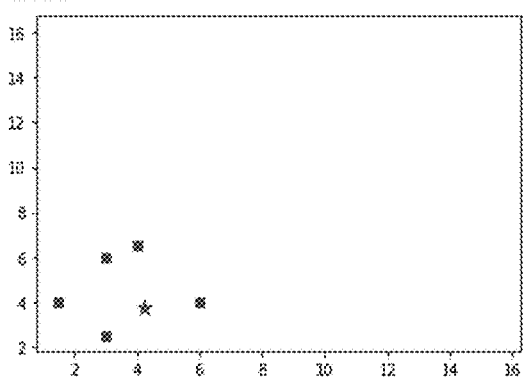
1006
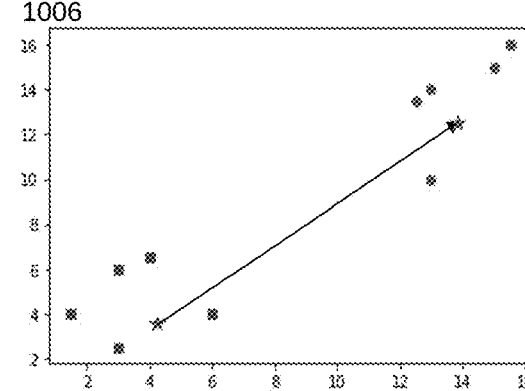
1007
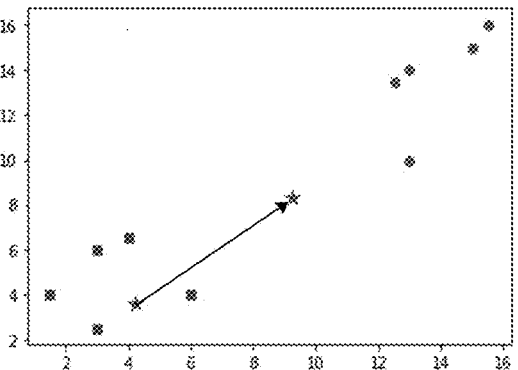
1008
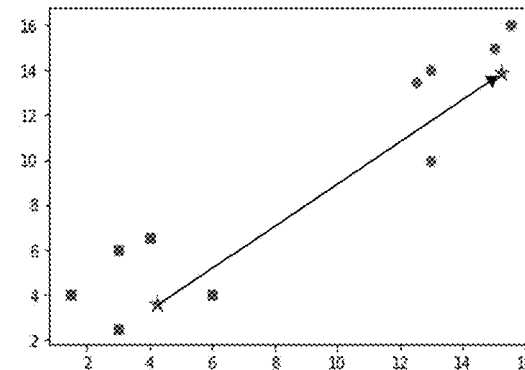

FIG. 11
1101
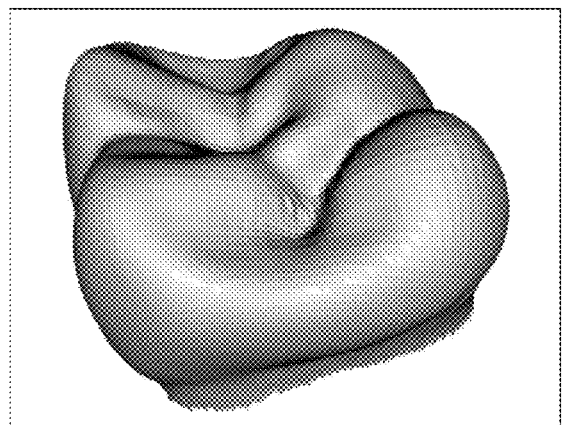
1102
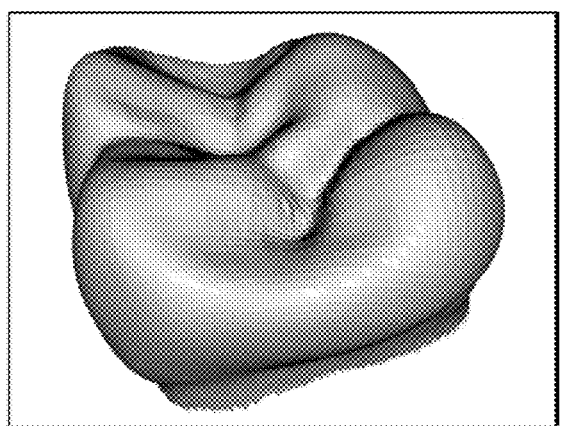
1103
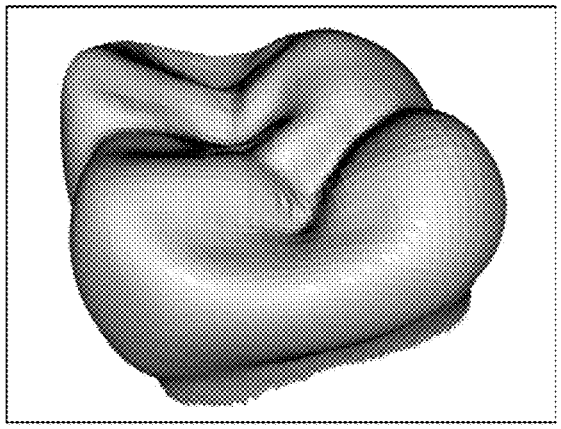
1104
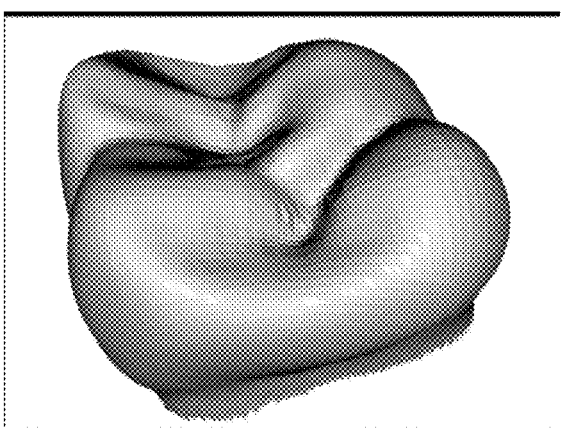
1105
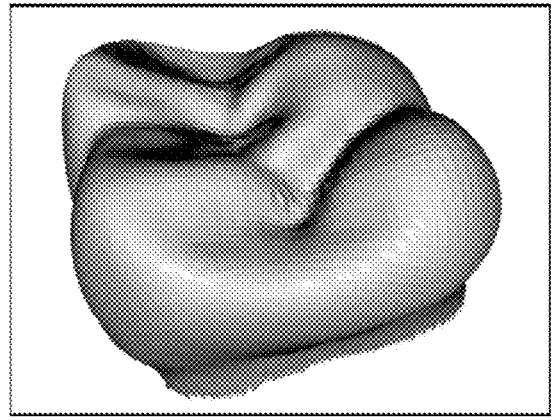

FIG. 12A
1201
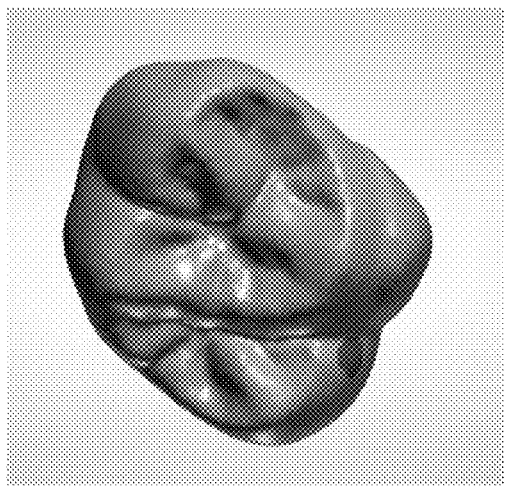
1202
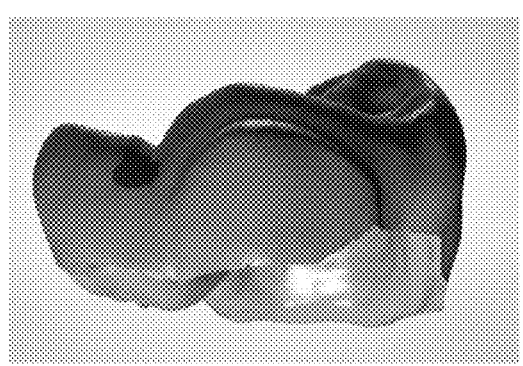
1203
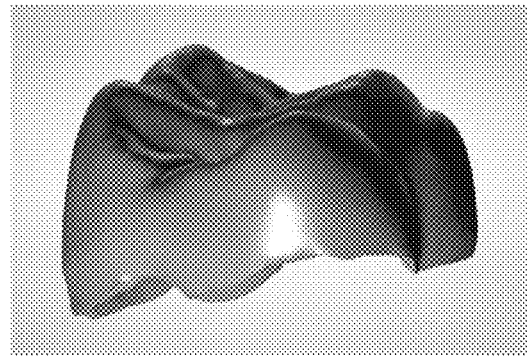
FIG. 12B
1204
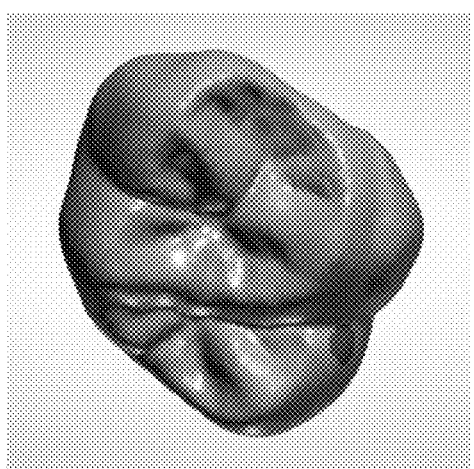
1205
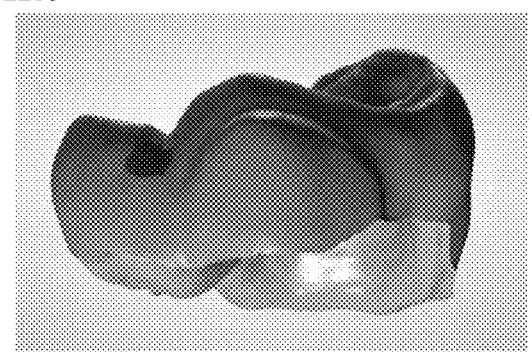
1206
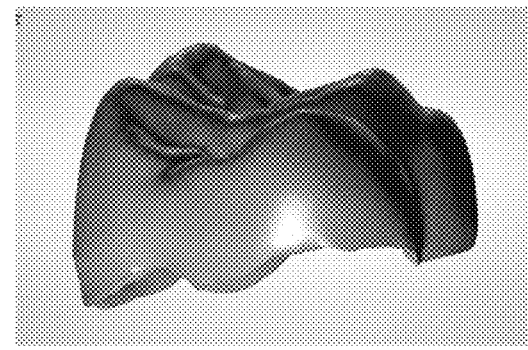

METHOD FOR GENERATING OBJECTS USING AN HOURGLASS PREDICTOR

CROSS-REFERENCE TO RELATED APPLICATIONS

The present application is a continuation of U.S. patent application Ser. No. 17/434,205, which was filed on Aug. 26, 2021, which is a national stage application of PCT/EP2020/054852, which was filed on Feb. 25, 2020, which claims the benefit of Danish Patent Application No. PA 2019 70132, which was filed on Feb. 27, 20219. The entire contents of U.S. patent application Ser. No. 17/434,205, PCT/EP2020/054852 and Danish Patent Application No. PA 2019 70132, are incorporated herein by reference.

FIELD OF THE INVENTION

This disclosure generally relates to a system and method for generating two-dimensional or three-dimensional objects, by means of an hourglass predictor that uses information from objects of similar type and related objects. Various embodiments of the disclosure relate to applying these methods to dental, orthodontic, and ear-related objects.

BACKGROUND OF THE INVENTION

Machine learning is useful for deriving information from large sets of data and using that data to generate new objects. However, many of the methods used to generate new objects use only objects of a similar type. These methods do not take into account related data that is not from the object itself, and thus, may be missing important considerations about the environment and other factors.

SUMMARY OF THE INVENTION

Disclosed is a computer-implemented method is configured to generate output data is disclosed. The method includes:
  training an autoencoder on a first set of training input data to identify a first set of latent variables and generate first set of output data, where the autoencoder comprises a first encoder, and a first decoder, where the first encoder converts the first set of input data into a first set of latent variables, where the first decoder converts the first set of latent variables to the first set of output data, where the first set of output data is at least substantially the same as the first set of training input data;
  training an hourglass predictor to return a second set of latent variables, where the hourglass predictor comprises a second encoder and the first decoder, where the second encoder converts a second set of training input data to the second set of latent variables, where the second set of latent variables has a comparable data format as the first set of latent variables, the first decoder converts the second set of latent variables into a second set of output data at least substantially the same as a set of training target data, and the second set of training input data is different from the first set of training input data; and
  using the hourglass predictor on a third set of input data to generate a third set of output data, where the third set of output data is a comparable data format to that of the first set of output data.

A typical machine learning approach generates new objects based on existing ones of the same type. For example, a dental crown may be generated by training a machine learning method on a large data set of existing dental crowns. However, a dental crown generated this way does not take into account the unique circumstances of the dental surroundings, for example, the space available. The hourglass predictor adds information from the dental surroundings to generate a crown similar to a crown a dental professional may have made for a unique set of dental surroundings. This embodiment is a single example of the flexibility of the hourglass predictor, as the hourglass predictor can be used with any related sets of input data.

The hourglass predictor may be configured to generate an object based not only on similar objects, but also related objects. For example, an embodiment uses the hourglass predictor to generate a dental crown based on dental surroundings from a dental patient. A crown is a type of dental restoration which caps or covers a tooth to restore it to normal shape, size, or function. Dental surroundings are the collection of objects around the crown or the preparation for the crown, including but not limited to: neighboring teeth, antagonist teeth, gingiva, jaw, and/or preparations. Currently, crowns are often made by hand or manually designed using CAD software, based on the judgment of a dental professional. This is time-consuming, and highly dependent on the individual judgment of the dental professional.

The first step in creating an hourglass predictor is to train an autoencoder. Autoencoders take input data, encode the input data into a set of latent variables, then decode the latent variables into output data, where the output data is at least substantially the same as the input data, as discussed below. They are frequently used for denoising applications, such as removing artefacts from digital photos. The object itself may be difficult to use as input data, and therefore, a representation of the object may be used instead. For example, a 2D image may represent a tooth.

One embodiment uses a variational autoencoder. A variational autoencoder is an autoencoder where the latent variables are generated from a probability distribution rather than directly from the encoder. Using the probability distribution allows for interpolation of the data, so that a reasonable estimate might be made where there is no similar input data. This probability distribution may be, for example, generated from a means and standard deviations vector or logarithms of variance.

To train an autoencoder, a first encoder converts a first set of training input data into a first set of latent variables, then a first decoder converts the first set of latent variables to a first set of output data. Both encoder and decoder may be neural networks. Examples of neural networks include but are not limited to convolutional neural networks and dense neural networks.

In an embodiment that relates to generating a dental crown, the crowns may be represented by a sampled matrix. The sampled matrix represents a 3D object, in a process discussed below. The sampled matrix enables neural networks to be applied to three-dimensional objects, and enables a plurality of three-dimensional objects be given consistent treatment such that they can be compared.

The autoencoder may use a plurality of sampled matrices as the first set of training input data. Each sampled matrix may be represented as a first set of latent variables. In this embodiment, there may be at least three latent variables, and each latent variable may be a scalar number. The first decoder then decodes each of the first set of latent variables back to a sampled matrix.

The training is complete when the first set of output data is at least substantially the same as the first set of input data.

In an embodiment where the autoencoder is used to generate dental crowns, this may be measured by mean distance between points on the surface of the generated dental crown and the original dental crown, and the threshold for sufficiently similar may be a mean distance of equal to or less than 0.1 mm.

Training the autoencoder enables the first set of latent variables to parametrize a type of object, and allows the latent variables to be decoded back into a sampled matrix, which corresponds to a representation of the underlying object.

An autoencoder by itself, however, only generates output data of the same type as the input data, and does not consider other constraints. For example, an autoencoder to create dental crowns may only generate dental crowns, without considering additional information such as the crown's neighboring teeth. The second step, training an hourglass predictor, allows the incorporation of additional information in generating new objects.

The hourglass predictor keeps the first decoder from the autoencoder, unchanged. However, it uses a second set of training data, where the second set of training input data is of a different but related underlying object as the first set of training data. Although these data sets may not be the same type of object, they may be related to each other, in that each has some information on the other. The training target data has the same type of underlying object as the first set of training input data.

For example, in an embodiment to make dental crowns, the second set of training input data is a set of sampled matrices derived from the dental surroundings of a crown or preparation site, and the training target data is a crown that is fitted to those surroundings. Having one set of data would tell us something about the other set of data, for example, the size of a crown designed for a particular set of surroundings would likely reveal something about the distance between neighboring teeth.

To train the hourglass predictor, the second set of training input data is encoded through a second encoder, to return a second set of latent variables. This second set of latent variables has the same data format as the first set of latent variables. In an embodiment to generate dental crowns, the data format of the sets of latent variables is a vector of scalar numbers. The second set of latent variables is then decoded by the first decoder to return a second set of output data, which has the same type of underlying object as the first set of output data. The second set of output data may at least substantially match the training target data. Note that these steps train the second encoder to return a second set of latent variables that can be decoded into objects of the same type as the first set of output data.

In an embodiment to generate a dental crown, the representation of the surroundings of the crown may be used to train the second encoder to return latent variables that decode into the crown. The training may be complete when the generated dental crown is at least substantially the same as the initial dental crowns, for example, by the same measure as described above for the step training the autoencoder.

Once the hourglass predictor is trained, it can be used to generate a third set of output data, of the same type of underlying object as first set of training input data, with a third set of input data of the same type of underlying object as the second set of training data.

For an embodiment generating a dental crown, this means that given a set of dental surroundings, a crown may be generated that predicts what a dental professional would have created for those dental surroundings. The hourglass predictor is flexible in application; as discussed below, it may be trained for different situations, generating different types of objects.

In an embodiment, the hourglass predictor may be used to generate a proposed digital 2D image of a desired dental setup based on a pre-treatment digital 2D image.

A desired dental setup represents a proposed dental setup for a patient and may be used for designing a dental restoration or planning an orthodontic treatment. The desired dental setup may be of proposed dental treatments, and may be based on actual cases designed by dental professionals. A proposed digital 2D image is a 2D image of a desired dental set up.

A pre-treatment digital 2D image is a digital image of a patient prior to treatment. It may be a 2D image that shows the smile of a patient wherein a part of the upper anterior teeth are visible.

In dental treatment, it is important to be able to give a patient an aesthetically pleasing smile while maintaining function. There are planning tools wherein the patient is presented with expected treatment results in order to enable the patient to visualize the resulting smile. The hourglass predictor in this embodiment may provide a means for doing so. For example, a dental professional may use a proposed 2D digital image of a desired dental set up to show a patient what her teeth will look like after a proposed course of treatment.

To train the autoencoder, the first set of input training data would be a set of proposed digital 2D images of desired dental setups. The 2D images may be direct 2D images such as photographs and/or renders of 3D models as 2D images such as 2D images based on a 3D scan. The similarity may be measured by a common measure for comparing digital images, e.g. the structural similarity index (SSIM) (Wang, Zhou, Eero P. Simoncelli, and Alan C. Bovik. "Multiscale structural similarity for image quality assessment." The Thirty-Seventh Asilomar Conference on Signals, Systems & Computers, 2003. Vol. 2. IEEE, 2003.)

To train the hourglass predictor, the second set of input training data would be a set of pre-treatment digital 2D images, for example, digital photographs of patients before treatment. The set of training target data may include a set of corresponding proposed digital 2D images of desired dental setups, e.g. digital 2D images of proposed or actual treatments for the cases from the pre-treatment digital 2D images. The similarity measure is similar to that for training the autoencoder.

Thus, the trained hourglass predictor may generate a proposed digital 2D image of a desired dental setup for new cases represented by pre-treatment digital 2D images, similar to those that would be designed by a dental professional. This automates work previously done manually by a dental professional, potentially saving time in treating dental patients. A dental professional may further modify the proposed digital 2D image of a desired dental setup, if needed.

An embodiment further comprises where the first set of latent variables and/or the second set of latent variables are used as a parametrization of the input data and/or output data.

A parameter can be used to both define and change the object it characterizes. For example, an object might be defined as having a height of 5 mm, but the height could be changed to 10 mm. Objects can be parametrized in Euclidean space, where they may be translated, scaled, rotated, sheared, reflected, mapped, and/or otherwise parametrized by various functions.

Beyond the traditional Euclidean parameters, machine learning methods may allow new and meaningful parameters based on information about the object. An hourglass predictor's latent variables are examples of such parameters. A set of latent variables define the shape of the object; at least one latent variable can also be used to change the shape of the object.

For example, a latent variable as parameter might be used to change the three-dimensional shape of a dental crown for a better bite, by changing several parts of the tooth at once. If the change is unsuccessful, the value of the parameter can simply be set back to its original value. Parameters also allow for optimization. As the object changes in accordance with the value of the parameter, the parameter can be changed until some aspect is optimized.

An embodiment further comprises where the first set of training input data, second set of training input data, the set of training target data, and/or third set of input data is based on a three-dimensional object, such as a three-dimensional scan of the 3D object.

A three-dimensional object is an object that exists in three dimensions. In various embodiments of this disclosure, three-dimensional objects include, but are not limited to: physical objects such as dental restorations and dentition, digital objects such as models of individual teeth and scans of physical objects such as dental restorations and ears.

An embodiment further comprises wherein the first set of training input data, the second set of training input data, the third set of input data, the set of training target data, the first set of output data, the second set of output data, and/or the third set of output data comprises one or more of the following: 2D image of the object, depth map, pseudo-image, point cloud, 3D mesh, and/or volumetric data.

Three-dimensional objects may be represented with both two-dimensional and three-dimensional representations.

Two-dimensional representations of three-dimensional objects include but are not limited to: depth maps, pseudo-images based on facet information, other multi-angle images.

Two-dimensional representations may be relatively easy to use in the hourglass predictor, as they are often images with a structure that can be directly used by encoder/decoder neural networks. For example, two-dimensional images may be comprised of an array of pixels, where pixels have a defined location in relation to the other pixels, and RGB or grayscale values that may be read as scalar numbers. The scalar numbers can be normalized, as well as undergo other procedures useful in pre-processing for neural networks.

Three-dimensional representations of three-dimensional objects include but are not limited to: volumetric representations, point clouds, primitive-based models, meshes.

Three-dimensional representations may also be used by the hourglass predictor, though their data formats may require some pre-processing before being used by a neural network. Three-dimensional machine learning can be a challenging problem in the art, as three-dimensional data formats may be to large to process efficiently and commonly used machine learning operations may not exist for three-dimensional data formats.

Volumetric representations, which are essentially three-dimensional pixels may be represented as a matrix format, where each element has three dimensions—the x, y, and z coordinates. Point clouds, which are collections of point in three-dimensional space, may be used through a system such as PointNet (Qi, Charles R., et al. "Pointnet: Deep learning on point sets for 3d classification and segmentation." *Proc. Computer Vision and Pattern Recognition (CVPR), IEEE* 1.2 (2017): 4.). Primitives may also be used as a neural network, for example, through at least one depth image and numbers that contain information about the configuration of the primitives (Zou, Chuhang, et al. "3d-prnn: Generating shape primitives with recurrent neural networks." 2017 *IEEE International Conference on Computer Vision (ICCV)*. IEEE, 2017).

A mesh is a collection of vertices, edges, and faces. Vertices are individual points representing the surface, edges are lines connecting the vertices, and faces are continuous areas surrounded by vertices and edges. Meshes may also be used in neural networks, either in a manner similar to point clouds, or by the process discussed below.

An embodiment further comprising a method wherein the first set of training input data, the second set of training input data, the third set of input data, the set of training target data, the first set of output data, the second set of output data, and/or the third set of output data is a corresponding 3D mesh, corresponding to a sampled matrix, wherein the sampled matrix is generated by a method comprising transforming an initial three-dimensional mesh into a planar mesh, the initial three-dimensional mesh comprising a first set of vertices and edges and the planar mesh comprising a second set of vertices and edges, wherein
- each vertex of the second set of vertices is a transformation of a vertex from the first set of vertices and comprises values of the vertex from the first set of vertices, and
- each edge of the second set of edges is a transformation of an edge from the first set of edges and comprises values of the edge from the first set of edges;
- sampling the planar mesh to generate a plurality of samples such that each sample from the plurality of samples comprises
- a three-dimensional coordinate comprising three numerical values representing a point in a three-dimensional space where the three numerical values are derived and/or taken directly from the initial three-dimensional mesh, and
- a coordinate comprising numerical values representing a position of the sample relative to other samples of the plurality of samples; and
- generating the sampled matrix based on the plurality of samples;
- representing the sampled matrix as a corresponding 3D mesh.

While three-dimensional meshes are a popular way to represent three-dimensional objects, they are difficult to use directly in many machine learning algorithms. Three-dimensional meshes are often non-uniform, with indefinite features, making it difficult to compare them directly by machine learning. Frequently-used machine learning operations such as convolutions may not exist for three-dimensional meshes. Further, computer-readable formats for three-dimensional meshes can be very large, requiring a lot of processing power to analyze.

An embodiment uses the hourglass predictor on three-dimensional meshes, via a corresponding 3D mesh to a sampled matrix. The method flattens three-dimensional meshes into two-dimensional meshes, representing them as matrices. Further, the matrices may be a uniform data format to represent different objects.

In various embodiments, the method may be particularly useful in generating dental, orthodontic, and ear-related objects, as discussed below.

Although some embodiments in this disclosure use three-dimensional meshes from three-dimensional scans, any three-dimensional mesh that can be embedded in a plane may be used.

An initial three-dimensional mesh may come from an open surface or a closed surface. Examples of an open surface include but are not limited to: the outer surface of a crown, a 3D scan of a tooth to the gingival margin, a 3D scan of a jaw. Examples of closed surfaces include but are not limited to: the entire surface of a crown, a three-dimensional model of a tooth, a 3D scan of an implant guide.

To flatten the initial three-dimensional mesh of to a planar mesh, a boundary should be set. In an embodiment with a three-dimensional object with an open surface, this boundary may be the open surface's boundary, a cut made along the surface, and/or a combination of the two.

In an embodiment with a three-dimensional object with a closed surface of genus zero, the boundary may be a single facet, or at least one cut along the surface. For closed surfaces, there may be an obvious place to cut, such as the edge between top and bottom. In a three-dimensional mesh of a tooth, places to cut include but are not limited to: anatomical features such as the gingival margin, the long axis of a tooth; geometric features such as the plane along a hemisphere; and/or any axes orthogonal to these.

Cutting a three-dimensional mesh may result in multiple planar meshes. This may be useful for capturing more details of the three-dimensional object.

The boundary of the surface of the three-dimensional object is then fixed to a boundary of a planar object. The planar object may be of different shapes, including but not limited to: triangles, quadrilaterals, circles, curved quadrilaterals including squircles, shapes based on the three-dimensional objects themselves.

Once the boundaries are fixed, the remaining vertices and edges are mapped to the planar object, flattening the initial three-dimensional mesh to a planar mesh. Various embodiments may use different methods for this mapping. Initially, a matrix of each vertex's connectivity to other vertices may be created, and solving the system of the matrix maps the coordinates of each vertex to the plane (Tutte, William Thomas. "How to draw a graph." *Proceedings of the London Mathematical Society* 3.1 (1963): 743-767). This connectivity may be weighted in different ways, resulting in different mappings. In various embodiments, these methods include but are not limited to: uniform weights (Tutte 1963), weights based on angles (Floater, Michael S., and Ming-Jun Lai. "Polygonal spline spaces and the numerical solution of the Poisson equation." *SIAM Journal on Numerical Analysis* 54.2 (2016): 797-824), weights based on cotangents (Meyer, Mark, et al. "Discrete differential-geometry operators for triangulated 2-manifolds." *Visualization and mathematics III*. Springer, Berlin, Heidelberg, 2003. 35-57).

For examples of flattening initial three-dimensional scans to planar meshes, see below.

Flattening the initial three-dimensional meshes in this manner allows for the initial three-dimensional mesh and the planar mesh to be bijective, meaning that each vertex can be mapped back and forth between the two meshes.

The planar mesh is then sampled, where each sample is a point on the planar mesh. The planar mesh can be sampled randomly, with a lattice, or a combination of the two.

Lattice sampling takes samples based on a lattice over the planar mesh. In various embodiments, lattices may be based on polar coordinates or rectangular coordinates, regular or irregular. A regular lattice has evenly spaced lines, such as a regular grid of squares or triangles. An irregular lattice lacks evenly spaced lines, and may be useful where information is unevenly distributed. For example, a planar mesh of the surface of a tooth with the boundary set at the gingival margin has more information at the center of the mesh than at the edges. Thus, an irregular lattice that gathers more samples from the center has more useful information about the tooth. For further examples, see below.

Samples based on a lattice may be taken from the intersections of the lines, different positions along the lines, or even from the cells of the lattice. Lattice sampling may be combined with random sampling, for example, choosing a random point from each lattice cell.

Each sample on the planar mesh has a corresponding three-dimensional Euclidean coordinate based on the initial three-dimensional mesh. If the sample is on a vertex, the Euclidean coordinate is identical to the vertex. If the sample is on an edge or face, the Euclidean coordinate is interpolated based on the vertices of the edge or face.

Each sample also has a location on the lattice. This lattice may be the basis for a sampled matrix, where each element of the matrix is a sample, and each element's location corresponds to the sample's lattice location. The sampled matrix may be regarded as a two-dimensional array with elements of three dimensions each, as three two-dimensional arrays with elements of one dimension each, or any other format that conveys both the samples' Euclidean coordinates and lattice location.

The sampled matrix can be visually represented as a two-dimensional red-green-blue matrix (2D RGB matrix). In the 2D RGB matrix, each matrix element's location is a sample's lattice location, and each matrix element's RGB value is the sample's Euclidean coordinates. The 2D RGB matrix is equivalent to the sampled matrix, and the two can be translated back and forth.

The sampled matrix may be analyzed using machine learning methods for two-dimensional data. This requires less computing power than similar methods for three-dimensional data. Further, there is a wider body of work on two-dimensional machine learning methods, potentially allowing novel methods that could not previously be applied to three-dimensional objects.

Because each element of the sampled matrix has a specific location in relation to its neighboring elements, machine learning methods requiring known neighboring elements can be applied. For example, convolutions pool several neighboring elements, to better capture the underlying information about an object and reduce the risk of chance variations changing the overall result. These are used in convolutional neural networks.

The sampled matrix also allows other improvements. The sampled matrix can represent an object with fewer data points, requiring less processing power. Further, the sampled matrix allows a uniform data format for non-uniform objects, permitting direct comparisons between 3D objects.

The disclosure further comprises representing the sampled matrix as a corresponding 3D mesh. As each element of the sampled matrix includes a three-dimensional point in Euclidean space, it can also be represented as a point cloud. Analyses done of the sampled matrix would also be analyses of the point cloud, and manipulations of the sampled matrix would have corresponding effects on the point cloud.

The point cloud can be reconnected into a three-dimensional mesh. While the point cloud can be reconnected in any way, a triangular mesh is typical for computer-aided design and manufacturing.

An embodiment further comprises where the third set of output data is used to estimate an unscanned and/or faultily scanned area.

The hourglass predictor may be used to estimate an unscanned and/or faultily scanned area. Often, getting a complete scan of an object is difficult, due to location, blocking objects, or the shape of the object itself. In such case, having a 3D model mesh to match to the scan allows the underlying object to be modelled regardless, as discussed below.

In an embodiment to estimate an unscanned and/or faultily scanned area, to train the autoencoder, the first set of training input data may be three-dimensional meshes of model objects. To train the hourglass predictor, the second set of training input data may use incomplete and/or faulty scans of an object of similar type, and the set of training target data may be 3D meshes corresponding to the incomplete and/or faulty scans of an object of similar type. Thus, the third set of output data may be three-dimensional meshes of model objects fitted to the incomplete and/or faulty scans. A dental example is discussed below.

An embodiment further comprises a method of estimating an unscanned and/or faultily scanned area wherein the unscanned and/or faultily scanned area is a dental area or an ear area.

In dental scans, a scan may be taken of a patient's teeth and jaw, for example, by using an intraoral scanner on the patient, or by scanning a gypsum model of the patient's oral situation. However, some areas of individual teeth may not be completely scanned, including but not limited to: interproximal areas, where neighboring teeth block the scanner; areas under brackets and other appliances, where the appliance blocks the scanner; subgingival areas, where the gingiva blocks the scanner. For facial scans, dental areas include areas behind facial features, where the lips might block the scanner. In these cases, the incomplete areas can be estimated with the hourglass predictor, using known teeth or library models as the initial model(s).

For example, for an incomplete scan of an incisor, the at least one unscanned and/or faultily scanned areas may be estimated with an hourglass predictor. In training the autoencoder, the first set of training input data may be a set of 3D representations of complete incisors, possibly taken from scans or digital models of complete incisors. The 3D representations of complete incisors may also be parametrized by the latent variables of the autoencoder.

In training the hourglass predictor, the second set of input data may be a set of 3D representations of incomplete and/or faulty scans of incisors. The set of training target data for this second set of input training data would be the corresponding set of 3D representations of complete incisors. A training data set may be artificially created, for example, by cutting away the parts of the incisors' surface that would be unscanned in a typical scan.

Training the hourglass predictor on this training data set results in an hourglass predictor that outputs estimates 3D representations of complete incisors, based on inputs of 3D representations of incomplete and/or faulty scans of incisors.

The third set of output data from the hourglass predictor may be used directly, or portions of it may be stitched together with existing scans.

The estimates of unscanned and/or faultily scanned areas may be used to simulate orthodontic treatments. Orthodontic treatment may move or rotate teeth, and tooth surfaces visible in the final result may not be initially scannable. The surfaces required include but are not limited to: interproximal areas, subgingival areas, dental roots, and/or any portion of combination of the above. Thus, estimates of unscanned and/or faultily scanned area for the teeth may be useful in simulating treatment.

An embodiment further comprises estimating at least one unscanned and/or faultily scanned ear area. Ear areas include but are not limited to: 1st bend, 2nd bend, anterior notch, antihelix, antitragus, concha, ear canal, ear canal including aperture, helix, intertragal notch, and/or tragus.

Scanning ears may be difficult. The size and curvature of the ear canal limits scanner size and range. Parts of the ear may be blocked by hair, cerumen, and/or other parts of the ear. Ears are not rigid, so the scanner or another object may deform the ear and affect the scan. Thus, it is helpful to have estimates of unscanned and/or faultily scanned areas of the ear to model what the ear scan should be, even if the original scan is incomplete or otherwise faulty.

An hourglass predictor for estimating ear scans, to train the autoencoder, may use as the first set of input data complete ear scans. To train the hourglass predictor, the second set of input training data may be incomplete and/or faulty ear scans, and the set of training target data may be the corresponding complete ear scans. These complete ear scans may come from laboratory scans of ear casts or a set of good scans. The process would be similar to the hourglass predictor for estimating incisors discussed above.

An embodiment further comprises using the hourglass predictor to design a dental restoration, orthodontic appliance, or ear-related device using at least one of the third set of output data, any portion thereof, and/or a combination thereof.

The dental restoration comprises one of more of the following: bridge, denture, crown, implant, implant guide, inlay, onlay, post and core, and/or veneer. The orthodontic appliance comprises one of more of the following: bracket guide, clear aligner, expander, lingual wire, and/or quad helix. The ear-related device comprises one of more of the following: fitted hearing aids, in-ear monitors, and/or noise protection devices.

By changing the training data, different types of object may be generated. For example, in an embodiment to generate a crown, the first set of training input data may be a plurality of crowns and/or teeth as models for veneers, the second set of training input data a plurality of the surroundings for crowns, and the set of training target data the crowns corresponding to those surroundings. A detailed example of generating a crown with an hourglass predictor is discussed below.

An embodiment further comprises using the hourglass predictor to identify non-movable objects in a three-dimensional scan, thereby allowing movable objects to be excluded from a three-dimensional scan.

When scanning a non-movable object to obtain a virtual 3D model of the non-movable object, movable objects may be captured in the sub-scans. For example, in scanning a dental patient's oral situation with a dental scanner, movable objects such as the patient's cheeks, tongue, or the dental professional's instruments or fingers may be included.

The goal is to use only surfaces from non-movable objects when generating the virtual 3D model, by differentiating between surfaces of movable objects and surfaces of non-movable objects.

An hourglass predictor for estimating non-movable objects may use as the first set of input data scans of known non-movable objects to train the autoencoder. To train the hourglass predictor, the second set of input training data may be scans of non-movable objects with movable objects, and the set of training target data may be the corresponding scans of non-movable objects. The corresponding scans of non-movable objects may be, for example, scans of a dental patients' jaws and dentition, and the scans of non-movable objects with movable objects may be the corresponding scans of the dental patient's jaw and dentition with movable objects such as tongues, fingers, cotton balls, etc. included. The process would be similar to the hourglass predictor for estimating incisors discussed above.

In some embodiments the non-movable object is a patient's oral situation. Movable object include but are not limited to: soft tissue that part of the patient's mouth, such as the inside of a cheek, the tongue, lips, gums and/or loose gingiva; dental instruments or remedies temporarily present in the patient's mouth, such as a dental suction device, cotton rolls, and/or cotton pads; fingers, such as a dental professional's finger.

An embodiment further comprises using the hourglass predictor to identify an object, a category of object.

As discussed above, the latent variables of the hourglass predictor may be a parametrization of a type of object. Therefore, the latent variables from an encoded object may be unique enough to distinguish that object from others of the same type.

In an embodiment, the hourglass predictor may be used to identify the category of tooth based on incomplete and/or faulty scans. To train the autoencoder, the first set of input training data may be 3D representations of complete teeth. To train the hourglass predictor, the second set of input training data may be 3D representations incomplete and/or faulty scans of teeth, and the set of training target data may be 3D representations of the corresponding 3D representations of complete teeth.

A set of 3D representations of complete teeth with labels for tooth types (incisors, bicuspids, molars, premolars, etc.) may then be run through the first encoder. The latent variables are kept and annotated with labels. Based on the values, range of values, and/or other characteristics of the latent variables, categories may be demarcated. When a new incomplete and/or faulty scan is encoded into latent variables with the second encoder, those latent variables can be compared to the categories, and a type of tooth identified.

In an embodiment, this may also be used to identify similar objects, for example, in previous scans from the same dental patient in a patient monitoring system for dental care. Only the autoencoder would be needed for this. A first set of training input data may be a set of jaw and dentition scans. The first encoder would be trained to encode these into a first set of latent variables. New input data, for example, a new scan of jaw and dentition, could then be encoded by the first encoder into a set of latent variables. The latent variables may be unique enough to identify a similar scan based on the new scan of jaw and dentition, especially compared to a plurality of latent variables of existing scans of jaw and dentition. The plurality of latent variables of existing scans of jaw and dentition may be based on a set of existing records at a dental office or lab.

Also disclosed is a computer-implemented method for transforming an object, comprising:

training an autoencoder on a set of training input data to identify latent variables and generate a set of training output data, where the autoencoder comprises an encoder, and a decoder, where the encoder converts training input data into latent variables, where the decoder converts latent variables to training output data, where the training output data is at least substantially the same as the training input data;

identifying a transformation vector with at least one data pair, where each of the at least one data pair comprises an initial object in an initial state and a transformed object in a transformed state, by: generating initial state latent variables for each initial object by using a representation of each initial object as input data for the encoder; generating transformed state latent variables for each transformed object by using a representation of each transformed object as input data for the encoder; identifying the transformation function based on the differences between the initial state latent variables and the transformed state latent variables; and transforming a new object with the transformation function by: generating new latent variables by using a representation of the new object as input data for the encoder; generating transformed new latent variables by applying the transformation vector and/or a function based on the transformation vector to the new latent variables; generating transformed output data by decoding the transformed new latent variables with the decoder.

In an embodiment, an object can be transformed into a modified version of itself by generating a transformation vector for the latent variables. By generating a transformation function from data pairs of initial objects and transformed objects, a new object may be transformed in a similar manner. This may be used, for example to predict aging in a tooth, as discussed below. A tooth would be "aged" with the transformation function derived from data pairs of original teeth and aged teeth. Further, an embodiment may use a vector as the transformation function, allowing the transformation function to act as a "slider" to age the tooth at different intervals, permitting a time-lapse view of what the tooth will look like as it ages.

An embodiment implementing this first trains an autoencoder to identify latent variables. The autoencoder may be trained by encoding training input data into latent variables, decoding the latent variables into training output data, and adjusting the weights of the encoder and decoder accordingly such that the training output data is at least substantially the same as the training input data. This procedure is discussed in more detail above.

After the autoencoder is trained, at least one data pair is used as input data for the encoder. A data pair comprises an initial object in an initial state, and a transformed object in a transformed state. Examples of data pairs include: an initial tooth and an aged tooth, an initial tooth and a tooth with raised cusps, an initial tooth and a tooth with increased angular symmetry.

The initial object and transformed object may need to be converted into a representation that can be used as input data for the encoder. For example, if the initial object is a tooth, it may need to be converted into a 3D mesh, and the 3D mesh converted into a numerical matrix before encoding. Examples of such representations are discussed above.

Next, a transformation function may be identified by comparing latent variables generated from the initial object and the transformed object. Initial state latent variables may be generated by inputting representation(s) of the initial object(s) into the encoder. Transformed state latent variables may be generated by inputting representation(s) of the transformed object(s) into the encoder. A transformation function is generated converting the initial state latent variables into the transformed state latent variables.

The transformation function may be, for example, a vector based on the average change between the latent variables of the data pair. A vector may be embodied as a list of numbers of the same length as the number of latent variables. A vector measures the difference between each initial state latent variable and the corresponding latent variable in the transformed state latent variables. Where there is more than one data pair, an average of these distances may be taken for each latent variable, where the averages make up the vector. This vector may then be added to a new set of latent variables, resulting in transformed new latent variables. An embodiment of such a vector is discussed below.

The transformation function may also, for example, be a linear or polynomial function converting the initial state latent variables to the transformed state latent variables. Examples include, where x represents the initial state latent variables, f(x) represents the transformed state latent variables, c represents some constant, and m represents a slope:

$$f(x) = mx + c$$
$$f(x) = mx^c$$

Once the transformation function is identified, it may then be used to transform a new object. A representation of the new object is used as input data for the encoder and encoded into new latent variables. The new latent variables are then transformed by the transformation function, and the transformed new latent variables are run through the decoder. The decoder then outputs the transformed new output data, which can be converted into a transformed new object.

An embodiment further comprises where the transformation function is a vector, and changing the vector controls the degree of transformation.

As discussed above, a vector may be a list of numbers. Thus, the vector may have simple operations performed on it, changing the values. For example, if the vector is halved, then applied to the initial state latent variables, the resulting transformed new object will be only partially transformed. If the vector is doubled, the resulting transformed new object will be transformed beyond the original. An embodiment where this is used to age the tooth is discussed below.

An embodiment further comprises where the initial object is an original tooth and the transformed object is an aged version of the original tooth.

In an embodiment, the transformation function may be used to age teeth. Teeth and dental objects wear down over time. Predicting how they age may aid in designing better dental devices from the outset. For example, a dental crown is typically expected to last 10 to 30 years. In designing a dental crown, it may be useful to predict how the crown and neighboring teeth will change over time.

In an embodiment, the initial object may be an original tooth and the transformed object may be an aged version of the original tooth. Representation(s) of the original tooth/teeth are used as input data in the encoder, generating initial state latent variables representing the original tooth/teeth. Also, representation(s) of the aged tooth/teeth are used as input data in the encoder, generating transformed state latent variables.

A transformation function may then be identified by comparing the difference between the transformed state latent variables and the initial state latent variables. As discussed above, this may be a vector, a linear function, and/or a polynomial function.

A new object, such as another tooth, may now be aged using the autoencoder and transformation function. Here, a representation of a new tooth or crown would be used as input data in the encoder, encoded into a set of latent variables, transformed by the transformation function, then decoded back into output data, with which a digital or physical object may be generated.

In an embodiment, where the transformation function is a vector, the vector may be used as a "slider" controlling the amount of aging. If each data pair is comprised of an original tooth and an aged version of the original tooth, and the original teeth are considered to be at year 0 and the aged teeth are at year 20, then the vector based on the average difference may be considered to age the teeth 20 years. A vector of the half the value may age the teeth 10 years; a vector of double the value may age the teeth 40 years; and so on, presuming a linear relationship between the vector an aging. Non-linear relationships may also be identified.

An embodiment further comprises where the initial state is that of an original tooth and the transformed state is a tooth with increased angular symmetry compared to the original tooth.

In an embodiment, the objects are teeth, the initial states of the teeth are original teeth, and the transformed state are teeth with increased angular symmetry. Increasing angular symmetry makes the tooth rounder, with less prominent major bumps. This allows the tooth to better fit neighboring teeth and optimize chewing.

A characteristic such as this is usually difficult to quantify; while angular symmetry is easy to calculate for a straight cylinder, a generated tooth needs to be realistic and tooth-like. This preserves the features that make the object tooth-like (e.g. bumps and fissures) while functionally allowing for control of how round the tooth is. Further, this can be done without careful calculation of rotational angles and surface changes; the data pairs used provide a series of examples, and the transformation function captures what the autoencoder learns about the change.

An embodiment further comprises output to a data format configured to manufacture a physical object from at least one of the third set of output data, any portion thereof, and/or any combination of the preceding.

Once a corresponding 3D mesh or transformed 3D mesh for an object has been generated, the mesh or a portion of it may be translated into a data format suitable for manufacture. In various embodiments, the generated 3D mesh may be a standard file type for 3D objects, including but not limited to: Collaborative Design Activity (COLLADA), Initial Graphics Exchange Specification (IGES), ISO 10303 (STEP), STL, Virtual Reality Modeling Language (VRML).

An embodiment further comprises generating a physical object from the corresponding 3D mesh, the transformed mesh, the 3D model mesh, any portion of the preceding meshes, and/or any combination of the preceding by 3D printing or milling.

The methods described in this invention are meant to be applied to the physical world. Milling and 3D printing are methods to turn a 3D mesh or 3D file format into a physical object. Milling is common in dentistry, since it allows durable, well-tested materials to be used. Dental mills carve out a 3D object that may require post-processing, such as curing. 3D printing is another method of generating physical objects, and one that is rapidly improving. It may allow custom objects to be made with less waste than traditional milling.

In this disclosure, the term data format has been used as is commonly used in mathematics and computer science, as the type of format used to store the relevant data. Examples of data formats include: scalars, vectors, vectors of scalar number, matrices, characters, strings, etc.

BRIEF DESCRIPTION OF THE DRAWINGS

The above, additional objects, and/or features of the present invention, will be further described by the following illustrative and non-limiting detailed description of embodiments of the present invention, with reference to the appended drawing(s), wherein:

FIG. 2 shows the method of creating an hourglass predictor, according to an embodiment;

FIG. 5 shows the hourglass predictor generating a proposed digital 2D image of a desired dental setup based on a pre-treatment digital 2D image, according to an embodiment;

FIG. 6A shows a depth map of a molar, in an embodiment;

FIG. 6B shows a pseudo-image of a molar, in an embodiment;

FIG. 6C shows a voxel representation of a molar, in an embodiment;

FIG. 6D shows a point cloud representation of the surface of a molar, in an embodiment;

FIG. 6E shows a mesh representation of the surface of a molar, in an embodiment;

FIG. 7 illustrates a method of generating a corresponding 3D mesh from a scan or a digital object, according to an embodiment;

FIG. 8A-8C shows the correspondence between a 2D RGB matrix, a sampled matrix, and a corresponding 3D mesh, according to an embodiment;

FIG. 8A shows grayscale images of the red, green, and blue matrices respectively, according to an embodiment;

FIG. 8B shows subsets of a sampled matrix, according to an embodiment;

FIG. 8C shows a corresponding 3D mesh to the sampled matrix in FIG. 8B and the images in FIG. 8A, according to an embodiment;

FIG. 10 shows Graphs 1001, 1002, 1003, 1004, 1005, 1006, 1007, and 1008, illustrating a simple example of a transformation function based on a vector;

FIG. 11 shows Images 1101, 1102, 1003, 1004, and 1005, illustrating an embodiment where a tooth is aged using a vector as a transformation function;

FIGS. 12A-12B show Images 1201, 1202, 1203, 1204, 1205, and 1206, illustrating an embodiment where the angular symmetry on the lingual side of a crown is increased with a transformation function;

FIG. 12A (Images 1201, 1202, and 1203) shows an original crown; and

FIG. 12B (Images 1204, 1205, and 1206) shows a transformed crown.

DETAILED DESCRIPTION

In the following description, reference is made to the accompanying figures, which show by way of illustration how the invention may be practiced.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

Figure 1:
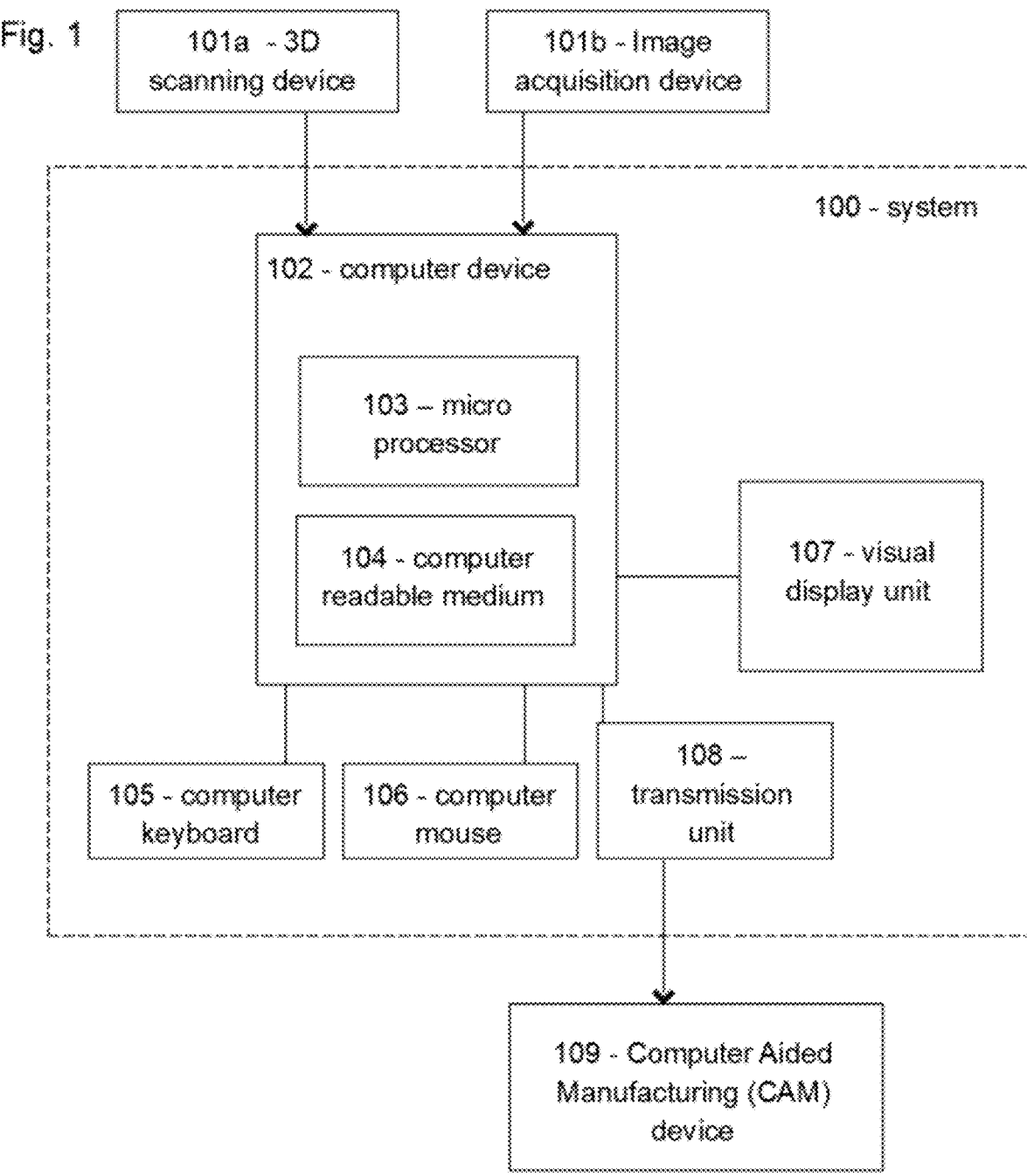
FIG. 1 shows a schematic of a system according to an embodiment of the disclosure.

FIG. 1 shows a schematic of a system according to an embodiment of the disclosure. The system 100 comprises a computer device 102 comprising a computer readable medium 104 and a microprocessor 103. The system further comprises a visual display unit 107, an input unit such as a computer keyboard 105 and a computer mouse 106 for entering data and activating virtual buttons visualized on the visual display unit 107. The visual display unit 107 may for example be a computer screen.

The computer device 102 is capable of obtaining digital representations, for example, of at least a part of a patient's jaw including the jawbone from e.g. a CBCT scanner 101b. The obtained digital representations can be stored in the computer readable medium 104 and provided to the processor 103.

Additionally or alternatively, the computer device 102 is further capable of receiving a digital 3D representation, for example, of the surfaces of the patient's set of teeth and gingiva from an image acquisition device 101a, for example a 3D scanning device, such as the TRIOS intra-oral scanner manufactured by 3shape TRIOS A/S, or capable of receiving scan data from such a 3D scanning device and forming a digital 3D representation of the patient's set of teeth and/or gingiva based on such scan data. The received or formed digital 3D representation can be stored in the computer readable medium 104 and provided to the microprocessor 103.

The system 100 is configured for allowing an operator to design a customized dental restoration using information obtained from the bone scan and/or the surface scan, with limits being set based on pre-determined design criteria. This can be realized for example by displaying the digital representation of the patient's jaw on the visual display unit 107, and the operator can then visualize his/her restoration design on the visual display unit, with respect to the surface of the patient's jaw.

The system comprises a unit 108 for transmitting the digital designs as an output data to a fabrication machine for generating a dental appliance, such as a customized dental restoration to e.g. a computer aided manufacturing (CAM) device 109 for manufacturing the customized dental restorations or to another computer system e.g. located at a milling or printing center where the customized dental restorations are manufactured. The unit for transmitting can be a wired or a wireless connection, and the transmission may be done for example using the internet or File Transfer Protocol (FTP).

The 3D scanning of the patient's set of teeth and/or gingiva using the 3D scanning device 101a, and/or the bone scan using the CBCT scanner 101b can be performed at a dentist while the designing of the customized dental restoration may be performed at a dental laboratory. In such cases the digital 3D representation of the patient's set of teeth and/or the 3D representation of the patient's jaw acquired from the CBCT scanner and/or scanning device can be provided via an internet connection between the dentist and the dental laboratory.

The system 100 as shown is an illustrative example. For example, the computer device 102 may comprise more than one micro processor 103 and/or more than one computer readable medium 104, the visual display unit 107 may be integrated in the computer device 102 or be separate from the computer device 102, etc.

FIG. 2 shows the method of creating an hourglass predictor, according to an embodiment. The hourglass predictor predicts what an object should be based on different but related data.

The first step is 200, training an autoencoder. In one embodiment, the first set of input training data 201 is the sampled matrix. The first encoder 202 encodes the first set of input training data 201 into a first set of latent variables 203. In one embodiment, the first encoder 202 is a neural network, for example, a convolutional neural network or a dense neural network.

The first set of latent variables 203 may have, for example, 3-50 latent variables in one embodiment, although there may be more or fewer latent variables. Latent variables can act as a parametrization of the tooth themselves, both for embodying the object, and for transforming the object. The latent variables are scalar numbers in one embodiment.

In one embodiment, the first decoder 204 is a neural network, including but not limited to: convolutional neural networks, dense neural networks. The first decoder 204 decodes the first set of latent variables 203 into a first set of output data 205. The first set of output data 205 has the same data format as the first set of training input data 201. In one embodiment, both 201 and 205 are sampled matrices.

A neural network is trained on target data, and the similarity between the output data and the target data determines what weights to assign to the neurons. Measuring the match between target data and output data was discussed above, in the summary. In an autoencoder, the training target data is the input data itself. Hence, the target data for the first set of output data 205 is the first set of training input data 206. The autoencoder is trained once the first set of output data 205 at least substantially matches the target data, i.e. the first set of training input data 201/206. The specific measure used to determine a substantial match depends on what the hourglass predictor is used for, but an example is given in FIG. 4.

The second step is 207, training an hourglass predictor. The second set of input data 208 has different underlying objects than the first set of input data. However, there should be an underlying connection between the objects represented by the first set of input data and the second set of input data, such that each object provides some information about the other. For example, a dental crown designed for a set of dental surroundings gives some information about the location of the neighboring and antagonist teeth, while a set of dental surroundings of a crown gives some information about the possible size and shape of the crown.

The data format of the second set of input data 208 may also be different from the first set of input data 201. Examples of underlying objects are in FIG. 4.

The second encoder 209 encodes the second set of input training data 208 into a second set of latent variables 210. In one embodiment, the second encoder 209 is a neural network, for example, a convolutional neural network or a dense neural network. The second set of latent variables 210 must be of the same data format as the first set of latent variables 203, including having the same number of latent variables and the same data type. However, because they come from a different set of data, they will have different values for the latent variables.

The first decoder 211 is identical to the first decoder 204 of the first step, and decodes the second set of latent variables 210 into the second set of output data 212. Because the first decoder 204/211 is used here, the second set of output data 212 has the same type of underlying object and the same data format as the first set of output data.

The set of target training data are generally of the same type of underlying object as the first set of training input data. The underlying objects represented in the training data sets are generally similar enough that they can be parametrized by the same set of latent variables, although they need not be identical. For example, outer surfaces of crowns and partial surfaces of teeth may be similar enough to be parametrized by the same set of latent variables, but are not identical underlying objects.

In training the hourglass predictor, each element of the set of target training data is matched to an element in the second set of training input data. The second set of output data 212 at least substantially matches to the training target data 213, and the second encoder may be weighted accordingly. Once the second set of output data 212 at least substantially matches the training target data 213, the hourglass predictor is trained. The exact measure for this match, as discussed above, depends on the application the hourglass predictor is used for.

The third step is 214, using the hourglass predictor. A third set of input data 215 and the second set of input data 208 have the same type of underlying object and the same data format. The second encoder 216 is identical to the second encoder 209 of the second step, and encodes the third set of input data 215 into a third set of latent variables 217.

The third set of latent variables 217 has the same data format as the first and second sets of latent variables 203 and 210.

The first decoder 218 is identical to the first decoder 204 and 211 of the first and second steps, and decodes the third set of latent variables 217 into the third set of output data 219. Because the first decoder 204/211 is used here, the third set of output data 219 has the same type of underlying object and the same data format as the first and second sets of output data 205 and 212.

The third set of output data 219 is a prediction of what the underlying object should be based on the third set of input data 215.

Figure 3:
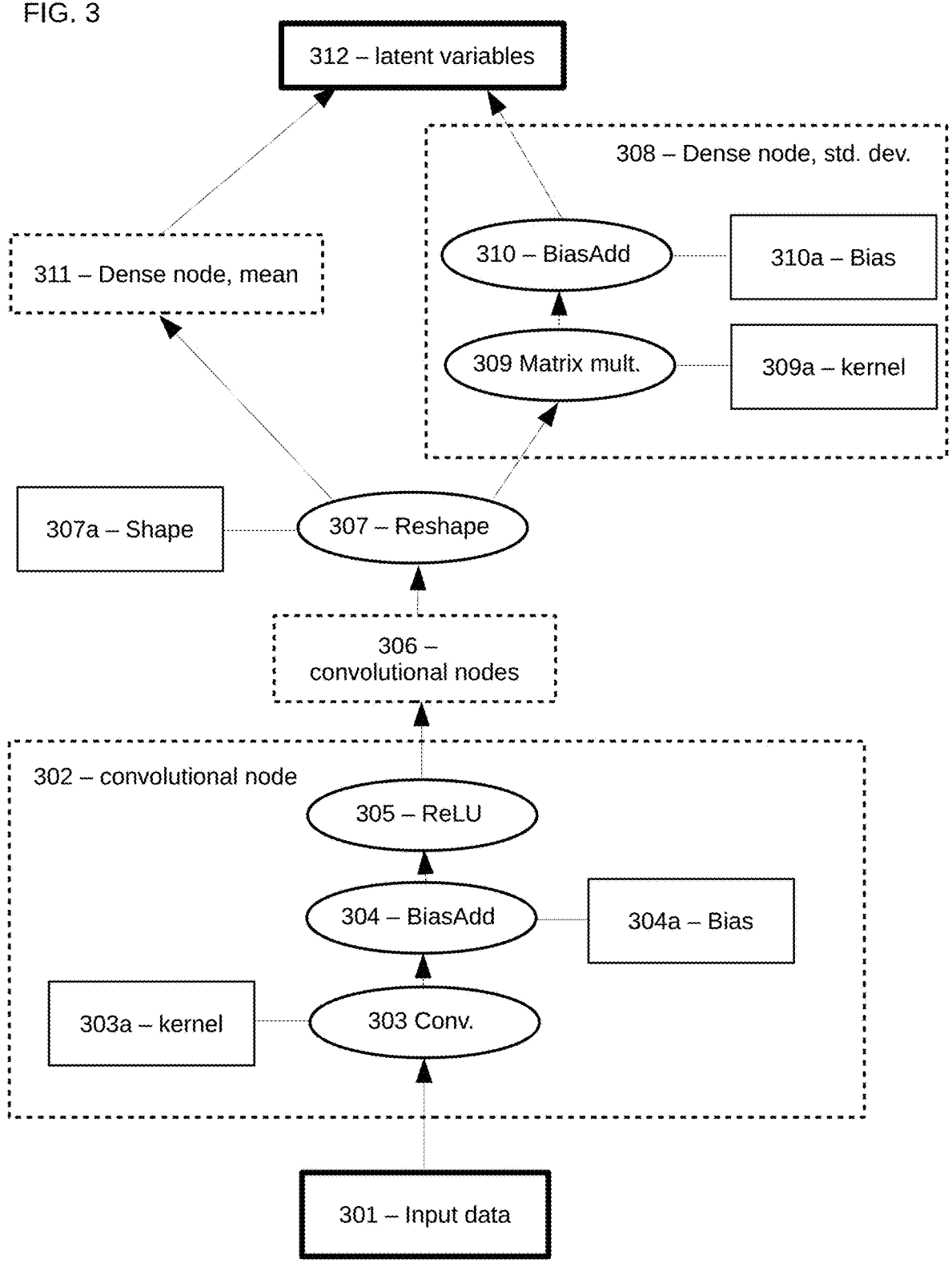
FIG. 3 shows an example architecture of a suitable convolutional neural network, according to an embodiment.

FIG. 3 shows an example architecture of a suitable convolutional neural network, according to an embodiment. This particular convolutional neural network may be used as an encoder. FIG. 3 is based off a tensorflow graph, commonly used to diagram neural networks.

The input data 301 is processed by a convolutional node 302. In this embodiment, the input data may be the sampled matrices of various crowns and/or teeth.

The convolutional node 302 may be comprised of a series of steps, for example: convolution 303, bias add 304, rectified linear unit 305.

Convolution 303 convolves the input data 301 with kernel 303a. Kernel 303a is a series of filters. Kernel 303a is a learnable parameter changed by backpropagation. The filters may be of any size of at least 2 by 2, but preferably size 4 by 4. There is at least one filter, but preferably a range of 16 to 512, and for this first convolution, more preferably 64. The filters may be randomly initialized. Convolution 303 uses strides of at least one, but preferably at least 2.

Convolution 303 outputs filter activations of the input data 301, which are then input into BiasAdd operation 304.

BiasAdd operation 304 takes the output of Convolution 303 and adds the bias 304a to each element. Bias 1006 is a set of scalar numbers. Bias 304a is a learnable parameter changed by backpropagation. Bias 304a may be randomly initialized or may be initialized at all zeros. BiasAdd operation 304 is optional for the convolutional node, but may be helpful in optimizing prediction results, depending on the embodiment.

The output of convolution 303 or the output of biasAdd operation 304 is then input into rectified linear unit (ReLU) 305. ReLU 305 is an activation function, which sets the input to zero if the input is negative, but does not change the input otherwise. Rectified linear units are a popular activation function, but other activation functions may be used, and include but are not limited to: sigmoid functions, hyperbolic tangents.

The output of ReLU 305 is a set of filter activation matrices, which may then be input into another convolutional node. Convolutional nodes 306 are a series of convolutional nodes of the same format as convolutional node 302, although their filter size, number of filters, filter initializations, stride size, biases, and activation functions may vary. Although convolutional node 302 may be sufficient for an embodiment of the network, more convolutional nodes are preferred. Thus, convolutional nodes 306 may be 1-24 convolutional nodes, preferably 4 convolutional nodes.

Reshape 307 takes the output of the final convolutional node of convolutional nodes 306 and changes the format with shape 307a. In this embodiment, shape 307a flattens each filter activation matrix from the output to a vector of scalar numbers. Flattening is necessary in this embodiment, as the next step is a dense node that requires a vector. However, other embodiments may use a different shape, depending on what input data format the next step requires.

The output vectors of Reshape 307 are then input into two dense nodes, a dense node A 308 and a dense B 311. Here, two dense nodes are used, because a variational autoencoder may require both means and standard deviations or logarithmic variance. However, another embodiment may use only one dense node or more than two dense nodes, to output latent variables directly.

Dense node A 308 may be comprised of a series of steps, for example: matrix multiplication 309, Bias add operation 310. Dense node A 308 may output standard deviations or logarithms of variance.

Matrix multiplication 309 multiplies its input data by a kernel 309a. Kernel 309a is a matrix of weights, which may be initialized randomly. Kernel 309a is a learnable parameter changed by backpropagation.

The output of matrix multiplication 309 is then input into bias add operation 310. Bias add operation 310 adds bias 310a to each element of the input. Bias 310a is a set of scalar numbers and a learnable parameter changed by backpropagation, and may be randomly initialized or may be initialized at all zeros.

Dense node B 311 has a similar format to dense node A 308, and may output means.

The output of dense nodes 308 and 311 is sampled to generate the latent variables 312. Although this embodiment of the invention uses two dense nodes, a single dense node may also be used to directly generate the latent variables 312.

These latent variables are then fed into a decoder, not pictured, which may be a similar neural network, but with deconvolutions rather than convolutions. The entire encoder-decoder structure is trained, backpropagating different weights to the various learnable parameters throughout the structure.

Figure 4:
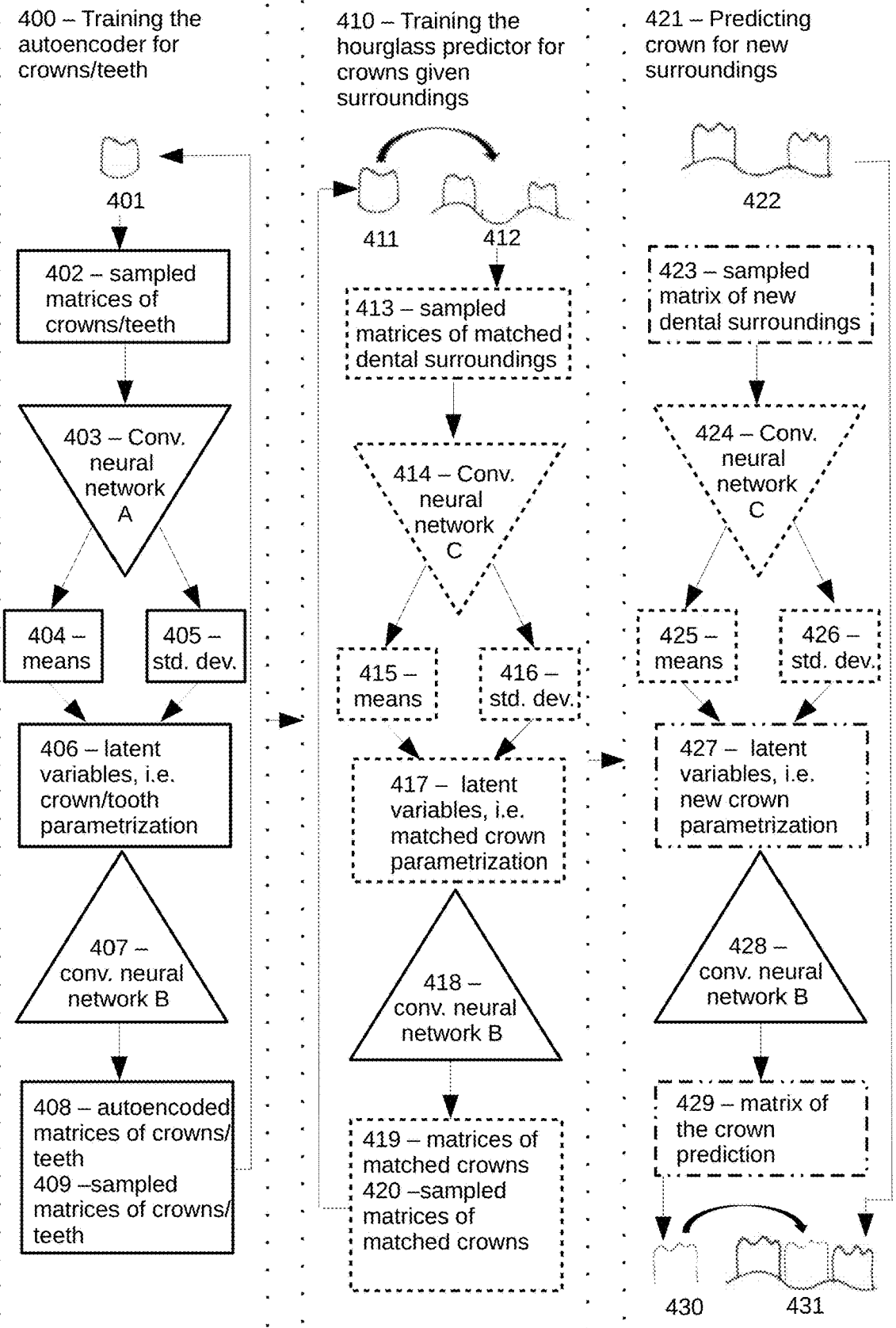
FIG. 4 shows the hourglass predictor generating a dental crown, according to an embodiment.

FIG. 4 shows the hourglass predictor generating a dental crown, according to an embodiment. In this embodiment, the hourglass predictor is trained to predict the outer surface of a dental crown given dental surroundings. The outer surface may be connected to a mesh of a bottom surface appropriate for further manufacture and/or the preparation. For FIG. 4, the term "crown" may be used as shorthand for the outer surface of a crown, in regards to objects 402, 408, 409, 419, 420, 429, and 430.

The first step 400 training an autoencoder to parametrize/output crowns. For the method of this embodiment, the autoencoder gives us a set of latent variables to parametrize the crown and a decoder to decode the latent variables back into a crown. In this embodiment, the autoencoder may be a variational autoencoder, which uses a probability distribution to generate latent variables rather than generating them directly (Goodfellow, Ian, et al. Deep learning. Vol. 1. Cambridge: MIT press, 2016, Chapter 14). An embodiment may also be an ordinary autoencoder, which generates latent variables directly. A variational autoencoder that uses the probability distribution allows better inferences where data is sparse.

Tooth 401 is one example of the type of underlying object represented by the input training data 402, the target training data 409, and the output data 408. A plurality of teeth and/or crowns are processed into sampled matrices per the method described in FIG. 7.

Sampled matrices of a plurality of crowns and/or teeth 402 are the first set of input training data. As the hourglass predictor is here being used only to generate the outer surface of a crown, both crowns and actual teeth may be used as training data. The sampled matrices of a plurality of crowns 402 may be based on scans of physical crowns and/or teeth, or digital objects representing crowns and/or teeth.

Convolutional neural network A (403) encodes the sampled matrices of a plurality of crowns 402 into a means vector 404 and a standard deviations vector 405. Vector 405 may alternatively be a vector of a logarithm of the variance. The means vector 404 and standard deviations vector 405 are then sampled to estimate latent variables, i.e. crown and/or tooth parametrization 406. An example of this convolutional neural network is further detailed in FIG. 3.

The latent variables, i.e. crown and/or tooth parametrization 406 can parametrize a tooth, and can be decoded back into a sampled matrix, with a corresponding 3D mesh for that tooth. The data format of these latent variables is a set of scalar numbers. There may be 3-50 scalar numbers, although the total number of set members should stay consistent for a given hourglass predictor.

The latent variables are a parametrization of the tooth, and allow the shape of the tooth to be represented by a set of scalar numbers. These numbers are not easily interpreted by human perception, but do contain information about the shape of the tooth as discovered by the machine learning method. Further, these numbers can be translated back into a corresponding 3D mesh of the underlying tooth.

As parametrizations, the latent variables can also be used to change the tooth. Changing the value of a latent variable comes with a corresponding change to the shape of the corresponding 3D mesh of the tooth. This allows for the precise quantification of change.

Convolutional neural network B (407) decodes the latent variables, i.e. crown and/or tooth parametrization 406 into autoencoded matrices of crowns/teeth 408. The autoencoded matrices of crowns/teeth 408 an embodiment of the first set of output data 205 in FIG. 2.

Convolutional neural networks use backpropagation for training, based on comparing output data to target data. Autoencoders are a special arrangement where the input data is itself the target data. Thus, the output data of convolutional neural network B (407), the autoencoded matrices of crowns/teeth 408, is evaluated based on its similarity to the sampled matrices of crowns/teeth 403/409.

The second step 410 trains the hourglass predictor to create crowns based on their surroundings. This step gives us an encoder to encode a different, but related set of input data into the latent variables. The latent variables can then be decoded back into the underlying object of the autoencoder. In this embodiment, the input data is a representation of the surroundings of a dental crown, and the output data is a representation of a dental crown.

The matched crown and surroundings 411 and 412 are an example of the underlying objects of the training data set for the hourglass predictor. The surroundings 412 are the collection of objects around the crown or the preparation for the crown, including but not limited to: neighboring teeth, antagonist teeth, gingiva, jaw, and/or preparations. The crown 411 is an existing crown designed for the surroundings 412, for example, by a dental technician.

The surroundings 412 are the underlying object for the input training data 413, and the crown 411 is the underlying object for the output data 419 and target training data 420. A plurality of these are processed into a sampled matrix per the method described in FIG. 7.

Sampled matrices of matched dental surroundings 413 are the second set of input training data. The sampled matrices of matched dental surroundings 413 are based on dental surroundings like 412 (See FIG. 7 for the method of obtaining a sampled matrix from a three-dimensional object).

Convolutional neural network C (414) encodes the sampled matrices of matched dental surroundings 413 into a means vector 415 and a standard deviations vector 416. The means vector 415 and standard deviations vector 416 are then sampled to estimate latent variables, i.e. matched crown/tooth parametrization 417. An example of a convolutional neural network is further detailed in FIG. 3.

The latent variables, i.e. matched crown parametrization 417, are of the same data format as the latent variables from the first step 406, and represent the same underlying objects.

Convolutional neural network B (418) decodes the latent variables, i.e. matched crown parametrization 417 into matrices of matched crowns 419. Convolutional neural network B (418) is identical to convolutional neural network B from the first step (407). Using convolutional neural network B (407/418) as decoder for both steps means that the latent variables are decoded into the same type of object, here the outer surface of a crown.

The matrices of matched crowns 419 are equivalent to the second set of output data 212 in FIG. 2. This output data is evaluated in comparison to the set of target training data, sampled matrices of matched crowns 420.

Each of the sampled matrices of matched crowns 420 corresponds to a sampled matrix of matched dental surroundings from 413. The decoder, convolutional neural network B (407/418) is not changed, meaning that a given set of latent variables always returns the same output. Thus, only the encoder, convolutional neural network C (414) is trained in step 410.

In sum, step 410 trains convolutional neural network C (414) to return latent variables (417) that will decode to crowns that match the given surroundings.

The third step 421 predicts a crown for new surroundings. The hourglass predictor, trained in the previous step, is used on a new set of dental surroundings to generate a crown. The generated crown is a prediction based on the training data from the previous step, and can be thought of as what a dental professional would have designed, given the surroundings.

New surroundings 422 are one example of the underlying object of the input data for the hourglass predictor. This is the same type of underlying object as the matched surroundings 412. The new surroundings 422 are processed into a sampled matrix 423 per the method in FIG. 7. The sampled matrix 423 is equivalent to the third set of input data 215 in FIG. 2.

Convolutional neural network C (424) encodes the sampled matrix of new dental surroundings 423 into a means vector 425 and a standard deviations vector 426. The means vector 425 and standard deviations vector 426 are then samples to estimate latent variables, i.e. matched crown/tooth parametrization 427. Convolutional neural network C (424) is identical to convolutional neural network C (414) from step 410.

The latent variables, i.e. new crown parametrization 427, are of the same data format as the latent variables from the first step (406) and second step (416), and represent the same underlying objects.

Convolutional neural network B (428) decodes the latent variables, i.e. new crown parametrization 427 into a sampled matrix of the crown prediction 429. Convolutional neural network B (428) is identical to convolutional neural network B from the first and second steps (407/418).

The matrix of the crown prediction 429 is equivalent to the third set of output data 219 in FIG. 2. Note that there is no training in step 421, so there is no target data, and no backpropagation.

The matrix of the crown prediction 429 can now be used to generate a physical crown 430. The matrix of the crown prediction 429 is reconnected into a mesh, and this mesh is connected to a mesh of a bottom surface appropriate for further manufacture and/or the preparation. If necessary, the mesh is converted a data format configured to manufacture a physical object, which is then used to mill, 3D print, or otherwise make the physical crown 430.

The physical crown 430 can be placed in the new surroundings 422, resulting in the new surroundings with crown 431.

FIG. 5 shows the hourglass predictor generating a proposed digital 2D image of a desired dental setup based on a pre-treatment digital 2D image, according to an embodiment. In this embodiment, the hourglass predictor is trained to predict the proposed digital 2D image given a pre-treatment digital 2D image.

The first step 500 trains an autoencoder to parametrize/output proposed digital 2D images. For the method of this embodiment, the autoencoder gives us a set of latent variables to parametrize the proposed digital 2D image and a decoder to decode the latent variables back into a proposed digital 2D image. In this embodiment, the autoencoder may be a variational autoencoder, as described above.

Desired dental set up 501 is one example of the type of underlying object represented by the input training data 502, the target training data 509, and the output data 508. Potential desired dental setups are discussed above.

The first set of input training data is a set of proposed digital 2D images of desired dental set ups 502. As proposed digital 2D images are an array of pixels, they may be represented by matrices. Each pixel may be represented as a matrix element, with values corresponding to the RGB or grayscale values of the proposed digital 2D image. These values may be normalized before further processing.

Convolutional neural network A (503) encodes the matrices of plurality of proposed digital 2D images 502 into a means vector 504 and a standard deviations vector 505, which are then sampled to generate the latent variables 506, in a process is similar step 400 of FIG. 4, described above. Vector 505 may use logarithmic variances in place of standard deviations.

The latent variables, i.e. proposed digital 2D image parametrization 506 can parametrize a proposed digital 2D image, and can be decoded back into a matrix with a corresponding 2D digital image. These latent variables have similar properties to the latent variables 406 in FIG. 4, in that they are scalar numbers with a range of values, and are parametrizations of the underlying object, as discussed above.

However, the underlying objects may be better represented by a different set of scalars, so the size of the set and optimal values may be different.

Convolutional neural network B (507) decodes the latent variables, i.e. proposed digital 2D image parametrization 506 into autoencoded matrices of proposed digital 2D images 508. The autoencoded matrices of proposed digital 2D images 508 are an embodiment of the first set of output data 205 in FIG. 2.

Convolutional neural networks require backpropagation for training, as discussed above. Thus, the output data of Convolutional neural network B (507), the autoencoded matrices of proposed digital 2D images 508, is evaluated based on its similarity to the matrices of proposed digital 2D images 503/509.

The second step 510 trains the hourglass predictor to create proposed digital 2D images based on corresponding pre-treatment digital 2D images.

The matched proposed digital 2D image 511 and matched pre-treatment digital 2D image 512 are an example of the underlying objects for the training data for the hourglass predictor. A pre-treatment digital 2D image is a digital image of a patient prior to treatment. It may be a 2D image that shows the smile of a patient wherein a part of the upper anterior teeth are visible.

The pre-treatment digital 2D image 512 is the underlying object for the input training data 513, and the proposed digital 2D image 511 is the underlying object for the output data 519 and target training data 520. The matrix representations are made is a similar manner to those discussed in step 500, training the autoencoder.

Convolutional neural network C (514) encodes the matrices of matched pre-treatment digital 2D image 513 into a means vector 515 and a standard deviations vector 516. The means vector 515 and standard deviations vector 516 are then samples to estimate latent variables, i.e. matched proposed digital 2D image parametrization 517. Vector 516 may use logarithmic variances in place of standard deviations.

The latent variables, i.e. matched proposed digital 2D image parametrization 517, are of the same data format as the latent variables from the first step 506, and represent the same underlying objects.

Convolutional neural network B (518) decodes the latent variables, i.e. matched proposed digital 2D image parametrization 517 into matrices of matched proposed digital 2D images 519. Convolutional neural network B (518) is identical to Convolutional neural network B from the first step (507). Using Convolutional neural network B (507/518) as decoder for both steps means that the latent variables are decoded into the same type of object.

The matrices of matched proposed digital 2D images 519 are equivalent to the second set of output data 212 in FIG. 2. This output data is evaluated in comparison to the set of target training data, matrices of matched proposed digital 2D images 520.

Each of the matrices of matched proposed digital 2D images 520 corresponds to a matrix of matched pre-treatment digital 2D image 513. The decoder, Convolutional neural network B (507/518) is not changed, meaning that only Convolutional neural network C (514) is trained in step 510, as discussed above.

In sum, step 510 trains Convolutional neural network C (514) to return latent variables (517) that decode to proposed digital 2D images that match the given pre-treatment digital 2D image.

The third step 521 predicts a proposed digital 2D image for new pre-treatment digital 2D image, and can be thought of as what a dental professional would have designed, for the pre-treatment digital 2D image.

The new pre-treatment digital 2D image 522 is an example of the underlying object of the input data for the hourglass predictor, of the same type as the matched pre-treatment digital 2D image 512. The new pre-treatment digital 2D image 522 is processed into a matrix 523 per the method discussed above.

Convolutional neural network C (524) encodes the matrix of new pre-treatment digital 2D image 523 into a means vector 525 and a standard deviations vector 526.

As described above, these are sampled to estimate latent variables, i.e. matched proposed digital 2D image/tooth parametrization 527. Convolutional neural network C (524) is identical to Convolutional neural network C (514) from step 510.

The latent variables, i.e. new proposed digital 2D image parametrization 527, are of the same data format as the latent variables from the first step (506) and second step (516), and represent the same underlying objects.

Convolutional neural network B (528) decodes the latent variables, i.e. new proposed digital 2D image parametrization 527 into a matrix of the proposed digital 2D image prediction 529. Convolutional neural network B (528) is identical to Convolutional neural network B from the first and second steps (507/518).

The matrix of the predicted proposed digital 2D image prediction 529 is equivalent to the third set of output data 219 in FIG. 2.

The proposed digital 2D image 530 can be incorporated in the new pre-treatment digital 2D image 522, for example, by superimposition, overlay, and/or combination, resulting in the new pre-treatment digital 2D image with predicted proposed digital 2D image 531.

FIG. 6A-6E show possible representations of 3D objects, in various embodiments.

Figure 6A:
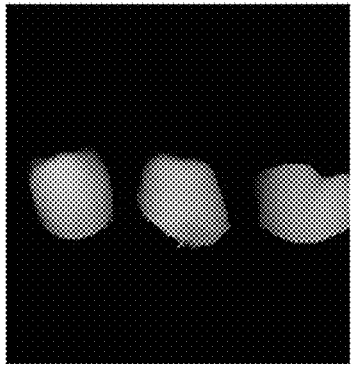
FIG. 6A-6E shows possible representations of 3D objects, in various embodiments.

FIG. 6A shows a depth map of a molar, in an embodiment. A depth map may be derived from a picture of a 3D object, where the scale of each pixel is used to estimate its distance from the camera, and therefore its representation in three-dimensional space. Here, the molar is shown from multiple viewpoints.

Figure 6B:
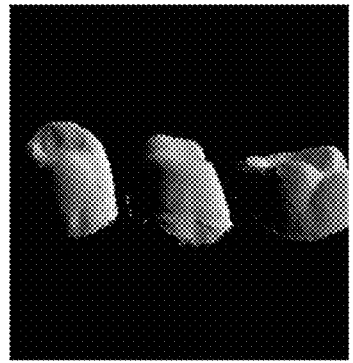

FIG. 6B shows a pseudo-image of a molar, in an embodiment. A pseudo-image is a 2D image where the grayscale value of each pixel represents the normalized distance of a viewpoint from the 3D object at that point. This distance may be derived from a 3D scan. Here, the molar is shown from multiple viewpoints.

Figure 6C:
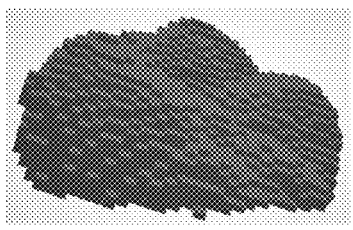

FIG. 6C shows a voxel representation of a molar, in an embodiment. Voxel representations use a three-dimensional grid to represent a 3D object. Each voxel may be a cube in a 3D space. If the object exists in that voxel, it is marked as present, and if not, it is absent. Here, a tooth is represented in voxels. Note that in this embodiment, the voxel size is especially large to more clearly illustrate the voxels. Smaller voxels may also be used, depending on the application.

Figure 6D:
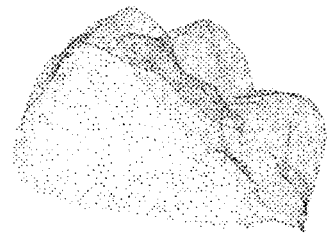

FIG. 6D shows a point cloud representation of the surface of a molar, in an embodiment. Point clouds are a collection of points in 3D space, each with an x, y, z coordinate. Here, the surface of the molar from FIG. 6C is shown as a point cloud, although a point cloud may represent the volume.

Figure 6E:
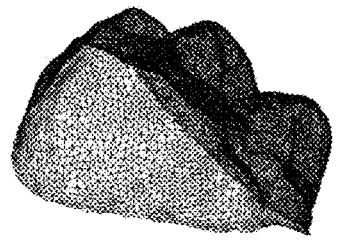

FIG. 6E shows a mesh representation of the surface of a molar, in an embodiment. A mesh is a collection of vertices, edges, and faces. Vertices are individual points representing the surface, edges are lines connecting the vertices, and faces are continuous areas surrounded by vertices and edges. Here, the surface of the molar from FIG. 6C-D is represented as a triangular mesh.

FIG. 7 illustrates a method of generating a corresponding 3D mesh from a scan or a digital object, according to an embodiment. In 701, a scan is taken of a physical object, here, the surface of a tooth or crown. This step is optional, as some objects exist solely as digital objects. A model may have been designed in a CAD/CAM program and never have been a physical object. 702 is an initial 3D mesh from the scan.

From 702 to 703, the initial 3D mesh is flattened to a planar mesh, through the mesh flattening procedure described above. At this point, the initial 3D mesh and the planar mesh are bijective. For some mesh flattening procedures, the flattening process may be entirely reversible. Step 704 shows the planar mesh being sampled, although, as discussed above, there are several methods to do this. Step 705 shows the sampled matrix, where each sample is interpolated or taken from a sample on the planar mesh.

Step 706 shows the corresponding 3D mesh to the sampled matrix according to an embodiment. Here, the corresponding mesh is a consistent mesh and the sampled matrix and corresponding 3D mesh can be translated back and forth. Further, an operation on either can be translated back to the other. For example, a matrix operation on the sampled matrix can translate to the corresponding 3D mesh. Conversely, a change of the shape of the corresponding 3D mesh in 705 can change the sampled matrix as well.

FIG. 8A-8C show the correspondence between a 2D RGB matrix, a sampled matrix, and a corresponding 3D mesh, according to an embodiment.

FIG. 8A shows grayscale images of the red, green, and blue matrices respectively, according to an embodiment. Image 800, the red matrix, represents the x-values of the samples from the planar mesh. Each pixel of the image is equivalent to a matrix cell of the matrix. The x-values have been normalized, and each pixel's scale value is its corresponding sample's normalized x-value. In a similar way, image 801, the green matrix, represents the y-values of the samples of the planar mesh, and image 802, the blue matrix, represents the z-values of the samples of the planar mesh.

The red, green, and blue matrices in FIG. 8A can be combined into a single colored image, the 2D RGB matrix (not displayed, as it would be a color image). The 2D RGB matrix combines the red, green and blue values from FIG. 8A, such that each pixel has an RGB value of the corresponding pixels from each of the matrices in FIG. 8A. A pixel's RGB value thus also corresponds to the three-dimensional coordinate of the pixel's corresponding sample.

FIG. 8B shows subsets of a sampled matrix, according to an embodiment. Specifically, they show rows 55-57, columns 1-3 of the sampled matrices. An entire sampled matrix is not shown due to the limited space available.

A sample from the planar mesh has a location and a three-dimensional coordinate. The location is a coordinate comprising numerical values representing a position of the sample relative to other samples. The three-dimensional coordinate comprising three numerical values representing a point in a three-dimensional space, and may be a Euclidean coordinate.

In the sampled matrices, the sample's location may be the location of its matrix element in the sampled matrix. The three-dimensional coordinate, expressed as x-, y-, and z-values, may be the value of the matrix element. This may be displayed in several ways, as three two-dimensional arrays with elements of one dimension (803-805), or as a two-dimensional array with elements of three dimensions (806).

The sampled matrix represented by 803 is a two-dimensional array with elements of one dimension, the x-dimension. Each matrix element represents a sample, where the matrix element's location is the sample's location, and the matrix element's value is the sample's x-value in absolute coordinates in millimeters. The sampled matrices represented by 804 and 805 are similar to 803, but for y-values and z-values respectively.

The sampled matrix represented by 806 is a two-dimensional array with elements of three dimensions. As can be seen by comparing the first element, an 806 matrix element's value is the value of the matrix elements at the same location in 803-805. Thus, 806 has all three coordinates, x, y, and z.

As the sampled matrix represented 806 and the sampled matrices represented by 803-805 are different data formats of the same object, both formats may be referred to as a "sampled matrix" in this document.

The sampled matrix represented by 803 is analogous to image 800, the red matrix. For a given sample, the x-value may be represented by the 800 matrix element's value as normalized to a color scale or the 803 matrix element's value as a Euclidean coordinate. Euclidean coordinates may be absolute or normalized; the matrices represented by FIG. 8B show absolute coordinates. The sampled matrix subset 803 is for rows 55-57, and columns 1-3, which correspond to the pixels in the same location in the red matrix 800.

In a similar way, the sampled matrices represented by 804 and 805 are analogous to 801 and 802 respectively.

The sampled matrix represented by 806 is analogous to the 2D RGB sampled matrix. For a given sample, the x, y, z value may be represented by the corresponding 2D RGB matrix element's value as normalized to an RGB scale, or the corresponding 806 matrix element's value as a Euclidean coordinate.

FIG. 8C shows a corresponding 3D mesh to the sampled matrix in FIG. 8B and the images in FIG. 8A, according to an embodiment. Note that, unlike a mesh from a scan, the corresponding 3D mesh in FIG. 8C is consistently connected. A vertex from the corresponding 3D mesh in FIG. 8C has a corresponding matrix element from sampled matrix represented by FIG. 8B; for example, the nine matrix elements shown in FIG. 8B are nine vertices along the left boundary of the tooth. The vertex also has a corresponding pixel in images FIG. 8A, here, the pixels in rows 55-57, columns 1-3.

The RGB matrix/matrices in FIG. 8A, the sampled matrices in FIG. 8B and the corresponding 3D mesh in FIG. 8C are different representations of the same underlying three-dimensional object. Further, these representations are bijective, and can be translated back and forth between formats.

By changing the properties of any one representation, the others can be changed. For example, a matrix operation to change the sampled matrix would change both the 2D RGB matrix and the corresponding 3D mesh. This is especially useful in applying machine learning methods, which rely on matrix operations and/or a uniform data set. The sampled matrix allows machine learning methods to be performed on three-dimensional objects.

In one embodiment, a scalar transformation may be done by multiplying each element of the matrix by a scalar number; the corresponding 3D mesh would change in size proportionate to the scalar number. In another embodiment, a principal component analysis could be performed on the sampled matrix. Any changes to the sampled matrix based on the principal components would also affect the corresponding 3D mesh.

Figure 9:
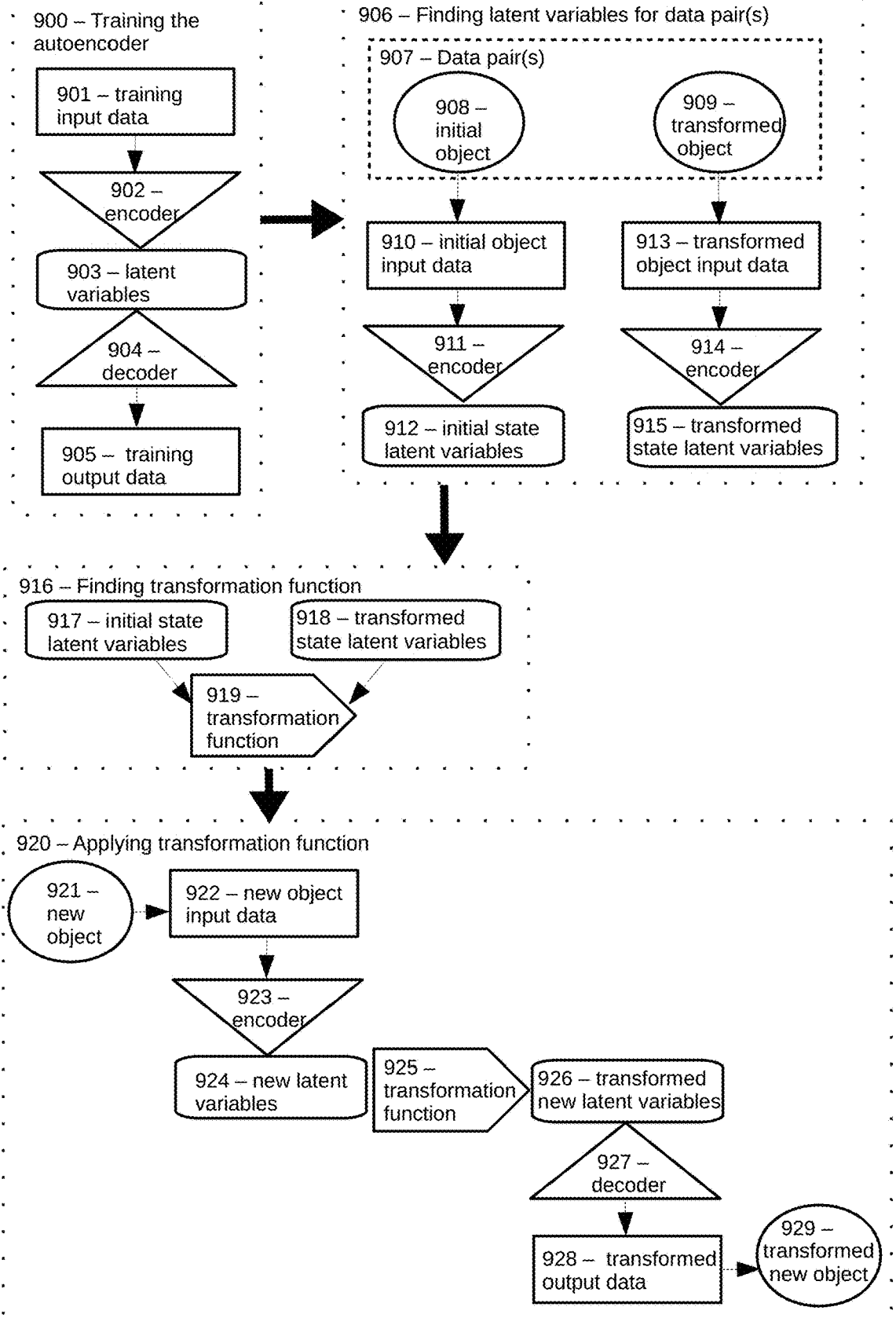
FIG. 9 shows an embodiment for a method of transforming an object using the transformation function.

FIG. 9 shows an embodiment for a method of transforming an object using the transformation function.

First, an autoencoder is trained in step 900. The details of training the autoencoder are similar to the autoencoder described in FIG. 2, step 200, but to summarize: Training input data 901 is encoded by the encoder 902 into latent variables 903. Latent variables 903 are decoded by the decoder 904 into training output data 905. Training output data 905 is then compared to training input data 901, and the weights of decoder 904 and encoder 902 are changed accordingly. This cycle repeats until training input data 901 and training output data 905 are substantially the same, at which point the autoencoder is considered trained.

Encoder 902 and decoder 904 may be neural networks; an example architecture is described in FIG. 3. Training input data 901 may be representations of real world objects, for example, flattened 3D meshes of teeth.

Next, latent variables are found for data pairs in step 906. As discussed above, each data pair 907 comprises an initial object 908 and a transformed object 909. These objects are similar to the type of object underlying the training input data 901, and thus can be read by the autoencoder from step 900. The initial object 908 and transformed object 909 are each run through the encoder 911/914, which is encoder 902 trained in step 900. Encoding outputs two sets of latent variables—initial state latent variables 912 and transformed state latent variables 915.

Step 916 finds a transformation 919 function based on initial state latent variables 917 and transformed state latent variables 918. Specific embodiments are discussed above and below.

Step 920 applies the transformation function 925 to a new object 921. The new object 921 may be of the same type as initial object 908, and may be converted into new object input data readable by the encoder 923. The encoder 923 is the same as encoder 911/914 from step 906 and the trained encoder 902 from step 900. Encoding the new object input data 922 generates new latent variables 924.

The new latent variables are then transformed by transformation function 925 into transformed new latent variables 926. Transformation function 925 is the transformation function 919 derived in step 916.

The transformed latent variables 926 are then decoded by decoder 927 into transformed output data 928. Decoder 927 is the same as the trained decoder 904 from step 900. Transformed output data 928 may be converted to transformed new object 929, which is new object 921 transformed in the same manner as the initial object 908 to the transformed object 909.

FIG. 10 illustrates a simple example of a transformation function based on a vector. It displays five data pairs with two latent variables each.

Graph 1001 of FIG. 10 shows 5 sets of initial state latent variables in an XY plot, each represented by a square, displaying two latent variables for each initial object. Although there may be more latent variables, only two are displayed here for ease of illustration, corresponding to the X and Y values of the plot. Similarly, give data pairs are displayed for illustrative purposes; training the autoencoder may involve more or fewer.

Graph 1002 of FIG. 10 further shows 5 sets of transformed state latent variables in an XY plot, each represented by a circle. Again, although there may be more latent variables, only two are displayed for ease of illustration, with values corresponding to the X and Y values of the plot. In this embodiment, the transformed state latent variables (circles) are clustered together away from the initial state latent variables (squares).

Graph 1003 of FIG. 10 further shows vectors, drawn as arrows, between the initial state latent variables (squares) and transformed state latent variables (circles) of each data pair. Vectors typically have a magnitude and a direction; in this embodiment, the vector's effect is to add a constant to each latent variable. Because the transformed state is considered the finished state, the vector direction points to the transformed state latent variables.

Graph 1004 of FIG. 10 further shows an embodiment of the transformation function, here the average vector (arrow) of the vectors of Graph 1003. Note that it starts at the center of the cluster of initial state latent variables (squares) and terminates at the center of the cluster of transformed state latent variables (circles). However, since a vector comprises a magnitude and direction, the vector need not start and terminate at the points displayed here. Rather, the vector is relative and may therefore applied to new sets of latent variables, which may be represented by new positions on the XY plot.

Graph 1005 of FIG. 10 further shows a new object's latent variables, represented by a star. In this embodiment, the new object is similar to the initial objects, as can be seen by its location in the cluster of initial object latent variables (squares).

Graph 1006 of FIG. 10 shows the transformation function, i.e. the vector (arrow) from Graph 1004, applied to the new object latent variables (star at beginning of arrow). The star at the end of the arrow is the transformed new latent variables. Note that the location of the transformed new latent variable is near the transformed latent variables (circles), indicating it is similar to those underlying objects.

Graph 1007 of FIG. 10 shows the use of the vector (arrow) for partial transformation. Here, the magnitude of the vector has been halved, and the transformed new latent variables (star at end of arrow) is now halfway between the initial object latent variables and the transformed object latent variables. This may be useful to adjust the level of transformation.

Graph 1008 of FIG. 10 shows the use of the vector (arrow) for over transformation. Here, the magnitude of the vector has been increased 20%, and so the transformed new latent variables (star at the end of the arrow) is extrapolated beyond the original transformation.

FIG. 11 shows an embodiment where a tooth is aged using a vector as a transformation function. Image 1101 of FIG. 11 is the new object, a molar. Image 1105 of FIG. 11 is the transformed new object, an aged molar, at 100% of the vector. Images 1102, 1103, and 1104 of FIG. 11 are transformed with the vector at 25%, 50%, and 75%, respectively.

FIG. 12 shows an embodiment where the angular symmetry on the lingual side of a crown is increased with the transformation function. FIG. 12A shows an original crown, and FIG. 12B show a transformed crown.

Increased angular symmetry may be desired in designing a crown, since a smoother crown is more comfortable for a patient and allows easier chewing. However, a perfectly round crown would not look like a real tooth, and would not fit well with the neighboring teeth. This results in the problem of adjusting a crown so that it looks like a realistic tooth, while minimizing certain undesirable features such as an overly protruding bump.

The transformation function can be used to solve this problem in a consistent and quantifiable way. FIG. 12A shows an original crown; FIG. 12B shows that crown transformed by a transformation function trained on a set of data pairs where the transformed object has increased angular symmetry on the lingual side.

Note that the original shape of the crown is generally maintained, but certain features have been smoothed down. For example, the large bump on the lingual side (as seen on the right side of the image in images 1201 and 1204 of FIG. 12) is slightly flatter. Although a subtle difference in the images, a patient can experience improved chewing and a more comfortable fit due to this change. As the transformation function was limited to the lingual side, however, the change does not affect neighboring teeth.

According to an embodiment, a computer program product embodied in a non-transitory computer readable medium is disclosed. The computer program product includes computer readable program code being executable by a hardware data processor to cause the hardware data processor to perform a method when said computer readable program code is executed by the hardware data processor. The method may include one or more functions that any of the system components to perform one or more steps of the method disclosed in one or more embodiments of this disclosure.

What is claimed is:

1. A computer-implemented method for generating an object based on output data, comprising
    training an autoencoder on a first set of training input data to identify a first set of latent variables and generate first set of output data, where the autoencoder comprises a first encoder, and a first decoder, where the first encoder converts the first set of input data into a first set of latent variables, where the first decoder converts the first set of latent variables to the first set of output data, where the first set of output data is at least substantially the same as the first set of training input data;
    training an hourglass predictor to return a second set of latent variables, where the hourglass predictor comprises a second encoder and the first decoder, where the second encoder converts a second set of training input data to the second set of latent variables, where the second set of latent variables has a comparable data format as the first set of latent variables, by the first decoder converts the second set of latent variables into a second set of output data at least substantially the same as a set of training target data, the set of training target data being generally of the same type of underlying object as the first set of training input data, and the second set of training input data is different from the first set of training input data; and
    using the hourglass predictor on a third set of input data to generate a third set of output data, where the third set of input data and the second set of input data have the same type of underlying object and the same data format, where the third set of output data is a comparable data format to the first set of output data, and
    generating the object based on the third set of output data, wherein the object is a dental restoration, an orthodontic appliance, an ear-related device or a proposed digital 2D image of a desired dental setup based on a pre-treatment digital 2D image.

2. The method according to claim 1, wherein the third set of input data contains information pertaining to objects surrounding the object to be generated.

3. The method according to claim 1, wherein sampled matrices of a plurality of crowns and/or teeth are the first set of input training data.

4. The method according to claim 1, where the first set of latent variables and/or the second set of latent variables are used as a parametrization of the input data and/or output data.

5. The method according to claim 1, where the first set of training input data, second set of training input data, the set of training target data, and/or third set of input data is based on a three-dimensional object, such as a three-dimensional scan of the 3D object.

6. The method according to claim 1, wherein the first set of training input data, the second set of training input data, the third set of input data, the set of training target data, the first set of output data, the second set of output data, and/or the third set of output data comprises one or more of the following: 2D image of the object, depth map, pseudo-image, point cloud, 3D mesh, and/or volumetric data.

7. The method according to claim 1, wherein the first set of training input data, the second set of training input data, the third set of input data, the set of training target data, the first set of output data, the second set of output data, or the third set of output data is a corresponding 3D mesh, corresponding to a sampled matrix, wherein the sampled matrix is generated by a method comprising:
    transforming an initial three-dimensional mesh into a planar mesh, the initial three-dimensional mesh comprising a first set of vertices and edges and the planar mesh comprising a second set of vertices and edges, wherein
    each vertex of the second set of vertices is a transformation of a vertex from the first set of vertices and comprises values of the vertex from the first set of vertices, and
    each edge of the second set of edges is a transformation of an edge from the first set of edges and comprises values of the edge from the first set of edges;
    sampling the planar mesh to generate a plurality of samples such that each sample from the plurality of samples comprises
    a three-dimensional coordinate comprising three numerical values representing a point in a three-dimensional space where the three numerical values are derived and/or taken directly from the initial three-dimensional mesh, and
    a coordinate comprising numerical values representing a position of the sample relative to other samples of the plurality of samples; and
    generating the sampled matrix based on the plurality of samples;
    representing the sampled matrix as a corresponding 3D mesh.

8. The method according to claim 1, where the third set of output data is used to estimate at least one unscanned and/or faultily scanned area.

9. The method according to claim 1, wherein the at least one unscanned and/or faultily scanned area wherein the at least one unscanned and/or faultily scanned area is a dental area or an ear area.

10. The method according to claim 1, further comprising designing the dental restoration, orthodontic appliance, or ear-related device using at least one of the third set of output data, any portion thereof, and/or a combination thereof.

11. The method according to claim 1, further comprising identifying non-movable objects in a three-dimensional scan, thereby allowing movable objects to be excluded from a three-dimensional scan.

12. The method according to claim 1, further comprising using the hourglass predictor to identify an object.

13. The method according to claim 1, further comprising output to a data format configured to manufacture a physical object from at least one of the third set of output data, any portion thereof, and/or any combination of the preceding.

14. The method according to claim 1, further comprising generating a physical object from the at least one of the third set of output data, any portion thereof, and/or any combination of the preceding by 3D printing or milling.

15. The method according to claim 1, wherein the first set of training input data, the second set of training input data, the third set of input data, the set of training target data, the first set of output data, the second set of output data, and the third set of output data is a corresponding 3D mesh, corresponding to a sampled matrix.

* * * * *